US012780892B2

(12) United States Patent
Lim et al.

(10) Patent No.: US 12,780,892 B2
(45) Date of Patent: Nov. 3, 2026

(54) LIQUID FORMULATION OF LONG-ACTING CONJUGATE OF GLUCAGON DERIVATIVE

(71) Applicant: HANMI PHARM. CO., LTD., Hwaseong-si (KR)

(72) Inventors: Hyung Kyu Lim, Hwaseong-si (KR); Joo Young Dong, Hwaseong-si (KR); Sang Yun Kim, Hwaseong-si (KR); Sung Min Bae, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 937 days.

(21) Appl. No.: 17/927,150

(22) PCT Filed: May 24, 2021

(86) PCT No.: PCT/KR2021/006441

§ 371 (c)(1),
(2) Date: Nov. 22, 2022

(87) PCT Pub. No.: WO2021/235907

PCT Pub. Date: Nov. 25, 2021

(65) Prior Publication Data

US 2023/0192800 A1 Jun. 22, 2023

(30) Foreign Application Priority Data

May 22, 2020 (KR) ........................ 10-2020-0061877

(51) Int. Cl.

| | |
|---|---|
| ***C07K 14/605*** | (2006.01) |
| ***A61K 47/10*** | (2017.01) |
| ***A61K 47/12*** | (2006.01) |
| ***A61K 47/26*** | (2006.01) |

(52) U.S. Cl.

CPC ............ *C07K 14/605* (2013.01); *A61K 47/10* (2013.01); *A61K 47/12* (2013.01); *A61K 47/26* (2013.01); *C07K 2319/30* (2013.01)

(58) Field of Classification Search

CPC ...... C07K 14/605; A61K 38/26; A61K 47/60; A61K 47/68; A61K 9/08

See application file for complete search history.

(56) References Cited

U.S. PATENT DOCUMENTS

| | | | | |
|---|---|---|---|---|
| 8,703,701 | B2 | 4/2014 | Dimarchi | |
| 10,696,725 | B2 * | 6/2020 | Kim | A61K 47/68 |
| 2017/0143802 | A1 * | 5/2017 | Kim | A61P 43/00 |
| 2018/0326013 | A1 * | 11/2018 | Kim | A61P 7/04 |

FOREIGN PATENT DOCUMENTS

| | | | | |
|---|---|---|---|---|
| AU | 2013342321 | A1 * | 5/2015 | A61P 43/00 |
| CN | 104519904 | A | 4/2015 | |
| CN | 109641035 | A | 4/2019 | |
| EP | 2 635 296 | B1 | 12/2014 | |
| KR | 10-2015-0035681 | A | 4/2015 | |
| KR | 10-2017-0003466 | A | 1/2017 | |
| KR | 10-2088863 | B1 | 3/2020 | |
| WO | 2007/021129 | A1 | 2/2007 | |
| WO | 2016/108586 | A1 | 7/2016 | |
| WO | 2017/003191 | A1 | 1/2017 | |

OTHER PUBLICATIONS

International Search Report for PCT/KR2021/006441 dated Sep. 27, 2021.

Communication dated Oct. 9, 2024 in Chinese Application No. 202180047534.8.

* cited by examiner

*Primary Examiner* — Gyan Chandra

(74) *Attorney, Agent, or Firm* — Sughrue Mion, PLLC

(57) ABSTRACT

A liquid formulation of a long-acting conjugate of glucagon, and a method for preparing the liquid formulation are disclosed. The liquid formulation contains 18 nmol/mL to 936 nmol/mL of a long-acting conjugate, a buffering agent in an amount for maintaining the pH of the liquid formulation in the range of 4.8 to 6.5, and 1.0% (w/v) to 20% (w/v) of a sugar alcohol, saccharide, or a combination thereof.

12 Claims, 2 Drawing Sheets

Specification includes a Sequence Listing.

[FIG. 1A]
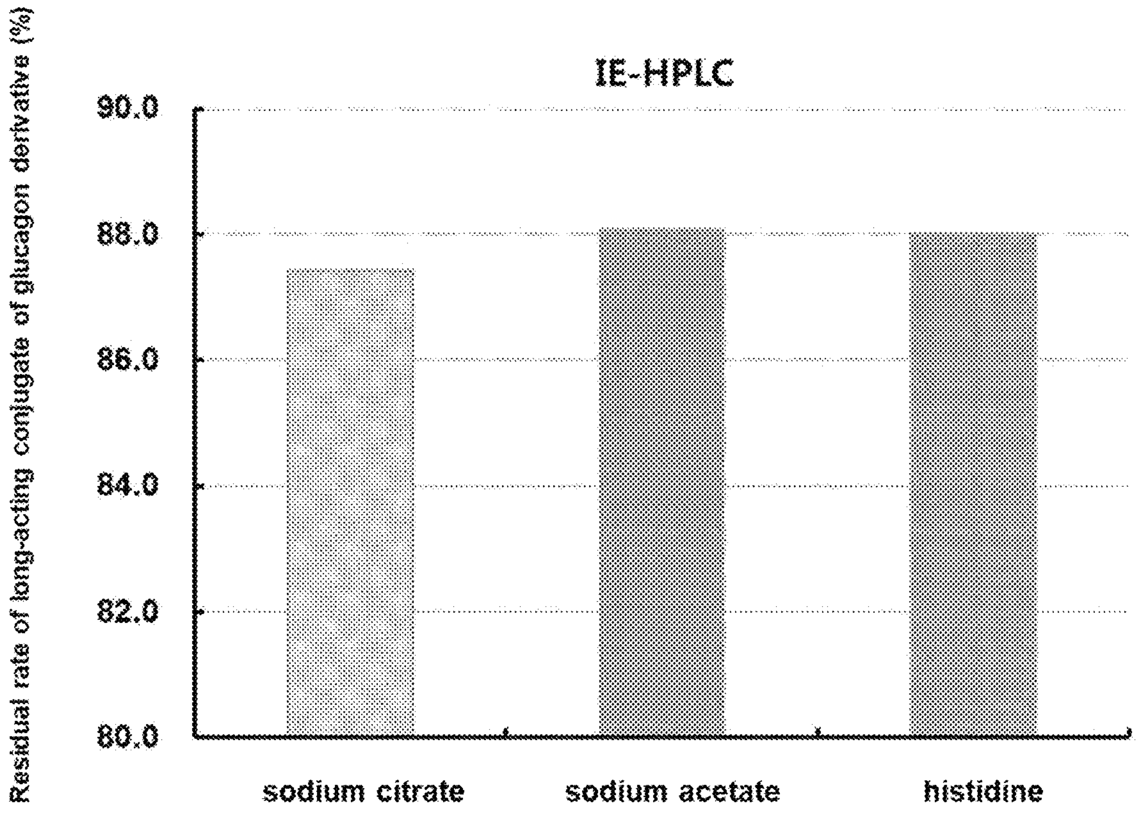

[FIG. 1B]
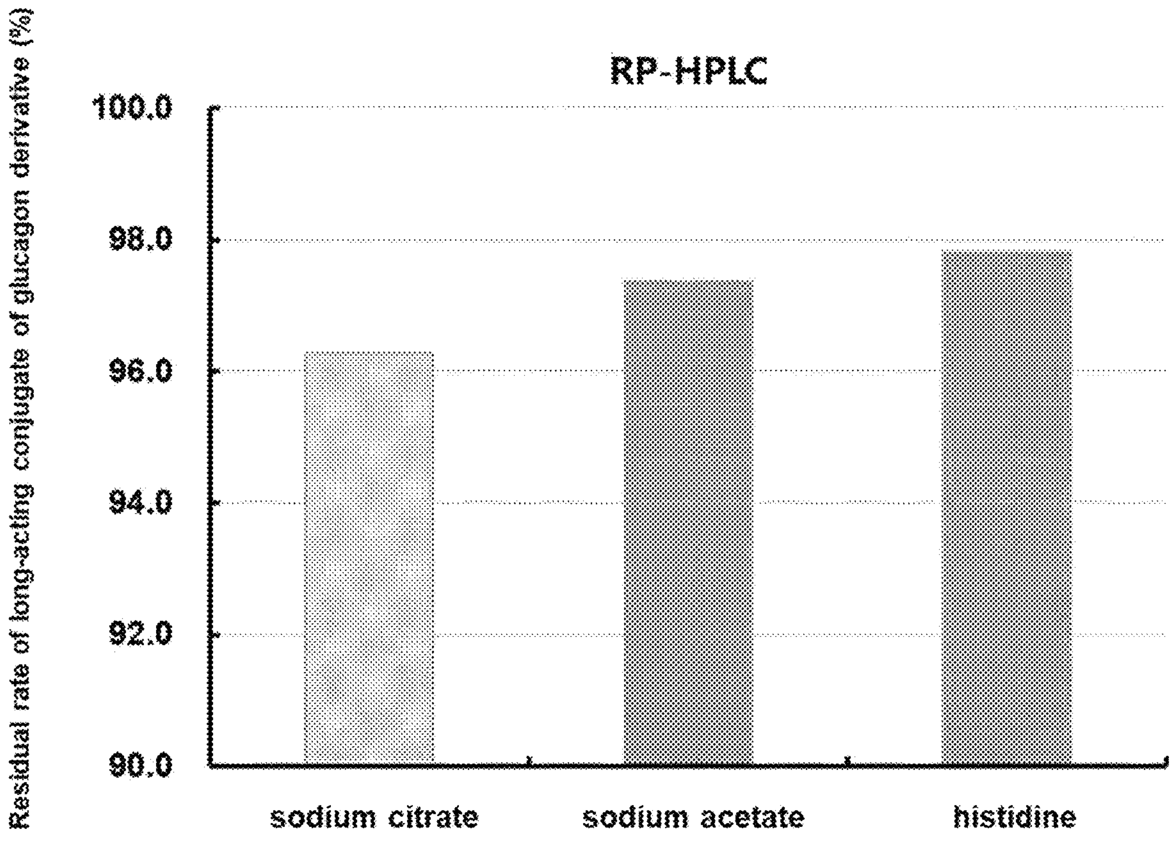

SEQUENCE LISTING

```
<160> NUMBER OF SEQ ID NOS: 70

<210> SEQ ID NO 1
<211> LENGTH: 29
<212> TYPE: PRT
<213> ORGANISM: homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25


<210> SEQ ID NO 2
<211> LENGTH: 29
<212> TYPE: PRT
<213> ORGANISM: Artificial Sequence
<220> FEATURE:
<223> OTHER INFORMATION: glucagon derivative

<400> SEQUENCE: 2

His Ser Gln Gly Thr Phe Thr Ser Asp Tyr Ser Lys Tyr Leu Asp Cys
1               5                   10                  15

Asp Arg Ala Gln Asp Phe Val Gln Trp Leu Met Asn Thr
            20                  25


<210> SEQ ID NO 3
<211> LENGTH: 29
<212> TYPE: PRT
<213> ORGANISM: Artificial Sequence
<220> FEATURE:
<223> OTHER INFORMATION: glucagon derivative

<400> SEQUENCE: 3

His Ser Gln Gly Thr Phe Thr Ser Asp Tyr Ser Lys Tyr Leu Asp Cys
1               5                   10                  15

Glu Arg Ala Gln Asp Phe Val Gln Trp Leu Met Asn Thr
            20                  25


<210> SEQ ID NO 4
<211> LENGTH: 29
<212> TYPE: PRT
<213> ORGANISM: Artificial Sequence
<220> FEATURE:
<223> OTHER INFORMATION: glucagon derivative

<400> SEQUENCE: 4

His Ser Gln Gly Thr Phe Thr Ser Asp Tyr Ser Lys Tyr Leu Asp Ser
1               5                   10                  15

Cys Asp Ala Gln Asp Phe Val Gln Trp Leu Met Asn Thr
            20                  25


<210> SEQ ID NO 5
<211> LENGTH: 29
```

<212> TYPE: PRT
<213> ORGANISM: Artificial Sequence
<220> FEATURE:
<223> OTHER INFORMATION: glucagon derivative

<400> SEQUENCE: 5

His Ser Gln Gly Thr Phe Thr Ser Asp Tyr Ser Lys Tyr Leu Asp Ser
1 5 10 15

Cys Glu Ala Gln Asp Phe Val Gln Trp Leu Met Asn Thr
20 25

<210> SEQ ID NO 6
<211> LENGTH: 29
<212> TYPE: PRT
<213> ORGANISM: Artificial Sequence
<220> FEATURE:
<223> OTHER INFORMATION: glucagon derivative

<400> SEQUENCE: 6

His Ser Gln Gly Thr Phe Thr Ser Asp Tyr Ser Lys Tyr Leu Asp Ser
1 5 10 15

Cys Glu Ala Asp Asp Phe Val Gln Trp Leu Met Asn Thr
20 25

<210> SEQ ID NO 7
<211> LENGTH: 29
<212> TYPE: PRT
<213> ORGANISM: Artificial Sequence
<220> FEATURE:
<223> OTHER INFORMATION: glucagon derivative

<400> SEQUENCE: 7

Tyr Ser Gln Gly Thr Phe Thr Ser Asp Tyr Ser Lys Tyr Leu Asp Ser
1 5 10 15

Cys Glu Ala Asp Asp Phe Val Gln Trp Leu Met Asn Thr
20 25

<210> SEQ ID NO 8
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

Tyr Xaa Gln Gly Thr Phe Thr Ser Asp Tyr Ser Lys Tyr Leu Asp Ser
1 5 10 15

Cys Asp Ala Gln Asp Phe Val Gln Trp Leu Ile Asn Thr
20 25

<210> SEQ ID NO 9
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

-continued

```
Tyr Xaa Gln Gly Thr Phe Thr Ser Asp Tyr Ser Lys Tyr Leu Asp Ser
1               5                   10                  15

Cys Asp Ala Gln Asp Phe Val Val Trp Leu Ile Asn Thr
            20                  25


<210> SEQ ID NO 10
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

Tyr Xaa Gln Gly Thr Phe Thr Ser Asp Tyr Ser Lys Tyr Leu Asp Ser
1               5                   10                  15

Cys Asp Ala Asp Asp Phe Val Val Trp Leu Ile Asn Thr
            20                  25


<210> SEQ ID NO 11
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 11

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25


<210> SEQ ID NO 12
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 12

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 13
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
```

<222> LOCATION: (2)
<223> OTHER INFORMATION: Xaa is aminoisobutyric acid (Aib)

<400> SEQUENCE: 13

Tyr Xaa Gln Gly Thr Phe Thr Ser Asp Tyr Ser Cys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 14

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 15

Tyr Xaa Gln Gly Thr Phe Thr Ser Asp Tyr Ser Lys Tyr Leu Cys Glu
1               5                   10                  15

Lys Arg Ala Gln Asp Phe Val Val Trp Leu Met Asn Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 16

Tyr Xaa Gln Gly Thr Phe Thr Ser Asp Tyr Ser Lys Tyr Leu Asp Cys
1               5                   10                  15

Arg Arg Ala Gln Val Phe Val Gln Trp Leu Met Arg Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: glucagon derivative
<220> FEATURE:

-continued

<221> NAME/KEY: MISC_FEATURE
<222> LOCATION: (2)
<223> OTHER INFORMATION: Xaa is aminoisobutyric acid (Aib)

<400> SEQUENCE: 17

Tyr Xaa Gln Gly Thr Phe Thr Ser Asp Tyr Ser Lys Tyr Leu Asp Cys
1               5                   10                  15

Val Arg Ala Gln Asp Phe Val Gln Trp Leu Met Arg Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 18

Tyr Xaa Gln Gly Thr Phe Thr Ser Asp Tyr Ser Lys Tyr Leu Asp Ser
1               5                   10                  15

Arg Arg Ala Cys Asp Phe Arg Leu Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 19

Tyr Xaa Gln Gly Thr Phe Thr Ser Asp Tyr Ser Lys Tyr Leu Cys Glu
1               5                   10                  15

Lys Arg Ala Lys Glu Phe Val Gln Trp Leu Met Asn Thr
            20                  25

<210> SEQ ID NO 20
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 20

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25

<210> SEQ ID NO 21
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

```
Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25
```

<210> SEQ ID NO 22
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

```
Tyr Xaa Gln Gly Thr Phe Thr Ser Asp Tyr Ser Lys Tyr Leu Asp Glu
1               5                   10                  15

Lys Arg Cys Lys Glu Phe Val Gln Trp Leu Met Asn Thr
            20                  25
```

<210> SEQ ID NO 23
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

```
Tyr Xaa Gln Gly Thr Phe Thr Ser Asp Tyr Ser Lys Tyr Cys Asp Glu
1               5                   10                  15

Lys Arg Ala Lys Glu Phe Val Gln Trp Leu Met Asn Thr
            20                  25
```

<210> SEQ ID NO 24
<211> LENGTH: 29
<212> TYPE: PRT
<213> ORGANISM: Artificial Sequence
<220> FEATURE:

-continued

<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

```
Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Met Asn Thr
            20                  25
```

<210> SEQ ID NO 25
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 25

```
Tyr Xaa Gln Gly Thr Phe Thr Ser Asp Tyr Ser Lys Tyr Leu Asp Glu
1               5                   10                  15

Lys Arg Ala Lys Cys Phe Val Gln Trp Leu Met Asn Thr
            20                  25
```

<210> SEQ ID NO 26
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 26

```
Trp Xaa Gln Gly Thr Phe Thr Ser Asp Tyr Ser Lys Tyr Leu Asp Glu
1               5                   10                  15

Cys Arg Ala Lys Asp Phe Val Gln Trp Leu Met Asn Thr
            20                  25
```

<210> SEQ ID NO 27
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 27

```
Tyr Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25
```

<210> SEQ ID NO 28
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 28

```
Trp Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25
```

<210> SEQ ID NO 29
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

```
Tyr Xaa Gln Gly Thr Phe Thr Ser Asp Tyr Ser Lys Cys Leu Asp Glu
1               5                   10                  15

Arg Arg Ala Lys Asp Phe Val Gln Trp Leu Met Asn Thr
            20                  25
```

<210> SEQ ID NO 30
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

```
Trp Xaa Gln Gly Thr Phe Thr Ser Asp Tyr Ser Lys Cys Leu Asp Glu
1               5                   10                  15
```

-continued

```
Arg Arg Ala Lys Asp Phe Val Gln Trp Leu Met Asn Thr
            20                  25


<210> SEQ ID NO 31
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (17)..(21)
<223> OTHER INFORMATION: amino acids at positions 17 and 21 form a ring

<400> SEQUENCE: 31

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25


<210> SEQ ID NO 32
<211> LENGTH: 28
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (15)..(19)
<223> OTHER INFORMATION: amino acids at positions 15 and 19 form a ring

<400> SEQUENCE: 32

Ser Gln Gly Thr Phe Thr Ser Asp Tyr Ser Lys Tyr Leu Asp Glu Cys
1               5                   10                  15

Arg Ala Lys Glu Phe Val Gln Trp Leu Met Asn Thr
            20                  25


<210> SEQ ID NO 33
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 33

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25


<210> SEQ ID NO 34
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
```

<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

Trp Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

Tyr Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

Tyr Xaa Gln Gly Thr Phe Thr Ser Asp Cys Ser Lys Tyr Leu Asp Glu
1               5                   10                  15

Arg Arg Ala Lys Glu Phe Val Gln Trp Leu Met Asn Thr
            20                  25

<210> SEQ ID NO 37
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

```
Tyr Xaa Gln Gly Thr Phe Thr Ser Asp Tyr Ser Lys Tyr Leu Asp Glu
1               5                   10                  15

Arg Arg Ala Lys Glu Phe Val Gln Trp Leu Met Asn Thr Cys
            20                  25                  30


<210> SEQ ID NO 38
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 38

Tyr Xaa Gln Gly Thr Phe Cys Ser Asp Tyr Ser Lys Tyr Leu Asp Glu
1               5                   10                  15

Arg Arg Ala Lys Glu Phe Val Gln Trp Leu Met Asn Thr
            20                  25


<210> SEQ ID NO 39
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 39

Tyr Xaa Gln Gly Thr Phe Val Ser Asp Cys Ser Lys Tyr Leu Asp Glu
1               5                   10                  15

Arg Arg Ala Lys Asp Phe Val Gln Trp Leu Met Asn Thr
            20                  25


<210> SEQ ID NO 40
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 40

Tyr Xaa Gln Gly Thr Phe Val Ser Asp Tyr Ser Lys Tyr Leu Asp Glu
1               5                   10                  15

Arg Arg Ala Lys Asp Phe Val Gln Trp Leu Met Asn Thr Cys
            20                  25                  30
```

<210> SEQ ID NO 41
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 41

```
Tyr Xaa Gln Gly Thr Phe Cys Ser Asp Tyr Ser Lys Tyr Leu Asp Glu
1               5                   10                  15

Arg Arg Ala Lys Asp Phe Val Gln Trp Leu Met Asn Thr
            20                  25
```

<210> SEQ ID NO 42
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 42

```
Tyr Xaa Gln Gly Thr Phe Cys Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 43
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 43

```
Tyr Xaa Gln Gly Thr Phe Thr Ser Asp Cys Ser Lys Tyr Leu Asp Ser
1               5                   10                  15

Arg Arg Ala Gln Asp Phe Val Gln Trp Leu Met Asn Thr
            20                  25
```

<210> SEQ ID NO 44
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 44

```
Tyr Xaa Gln Gly Thr Phe Thr Ser Asp Tyr Ser Lys Tyr Leu Asp Ser
1               5                   10                  15
```

```
Arg Arg Ala Gln Asp Phe Val Gln Trp Leu Met Asn Thr Cys
            20                  25                  30


<210> SEQ ID NO 45
<211> LENGTH: 29
<212> TYPE: PRT
<213> ORGANISM: Artificial Sequence
<220> FEATURE:
<223> OTHER INFORMATION: Glucagon analog
<220> FEATURE:
<221> NAME/KEY: MISC_FEATURE
<222> LOCATION: (2)
<223> OTHER INFORMATION: Xaa = aminoisobutyric acid (Aib)

<400> SEQUENCE: 45

Tyr Xaa Gln Gly Thr Phe Thr Ser Asp Tyr Ser Cys Tyr Leu Asp Glu
1               5                   10                  15

Lys Arg Ala Lys Glu Phe Val Gln Trp Leu Met Asn Thr
            20                  25


<210> SEQ ID NO 46
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (1)
<223> OTHER INFORMATION: Xaa is histidine, desamino-histidyl,
      N-dimethyl-histidyl, beta-hydroxy imidazopropionyl,
      4-imidazoacetyl, beta-carboxy imidazopropionyl, tryptophan, or
      tyrosine, or is absent
<220> FEATURE:
<221> NAME/KEY: MISC_FEATURE
<222> LOCATION: (2)
<223> OTHER INFORMATION: Xaa is alpha-methyl-glutamic acid,
      aminoisobutyric acid (Aib), D-alanine, glycine, Sar
      (N-methylglycine), serine, or D-serine
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (13)
<223> OTHER INFORMATION: Xaa is tyrosine or cysteine
<220> FEATURE:
<221> NAME/KEY: MISC_FEATURE
<222> LOCATION: (14)
<223> OTHER INFORMATION: Xaa is leucine or cysteine
<220> FEATURE:
<221> NAME/KEY: MISC_FEATURE
<222> LOCATION: (15)
<223> OTHER INFORMATION: Xaa is aspartic acid, glutamic acid, or
      cysteine
<220> FEATURE:
<221> NAME/KEY: MISC_FEATURE
<222> LOCATION: (16)
<223> OTHER INFORMATION: Xaa is glutamic acid, aspartic acid, serine,
      alpha-methyl-glutamic acid, or cysteine, or is absent;
<220> FEATURE:
<221> NAME/KEY: MISC_FEATURE
<222> LOCATION: (17)
<223> OTHER INFORMATION: Xaa is aspartic acid, glutamine, glutamic acid,
      lysine, arginine, serine, cysteine, or valine, or is absent
```

-continued

<220> FEATURE:
<221> NAME/KEY: MISC_FEATURE
<222> LOCATION: (18)
<223> OTHER INFORMATION: Xaa is alanine, aspartic acid, glutamine, glutamic acid, arginine, valine, or cysteine, or is absent
<220> FEATURE:
<221> NAME/KEY: MISC_FEATURE
<222> LOCATION: (19)
<223> OTHER INFORMATION: Xaa is alanine, arginine, serine, valine, or cysteine, or is absent
<220> FEATURE:
<221> NAME/KEY: MISC_FEATURE
<222> LOCATION: (20)
<223> OTHER INFORMATION: Xaa is lysine, histidine, glutamic acid, glutamine, aspartic acid, arginine, alpha-methyl-glutamic acid, or cysteine, or is absent
<220> FEATURE:
<221> NAME/KEY: MISC_FEATURE
<222> LOCATION: (21)
<223> OTHER INFORMATION: Xaa is aspartic acid, glutamic acid, leucine, valine, or cysteine, or is absent
<220> FEATURE:
<221> NAME/KEY: MISC_FEATURE
<222> LOCATION: (23)
<223> OTHER INFORMATION: Xaa is isoleucine, valine, or arginine, or is absent
<220> FEATURE:
<221> NAME/KEY: MISC_FEATURE
<222> LOCATION: (24)
<223> OTHER INFORMATION: Xaa is valine, arginine, alanine, cysteine, glutamic acid, lysine, glutamine, alpha-methyl-glutamic acid, or leucine, or is absent;
<220> FEATURE:
<221> NAME/KEY: MISC_FEATURE
<222> LOCATION: (27)
<223> OTHER INFORMATION: Xaa is isoleucine, valine, alanine, lysine, methionine, glutamine, or arginine, or is absent
<220> FEATURE:
<221> NAME/KEY: MISC_FEATURE
<222> LOCATION: (28)
<223> OTHER INFORMATION: Xaa is glutamine, lysine, asparagine, or arginine, or is absent
<220> FEATURE:
<221> NAME/KEY: MISC_FEATURE
<222> LOCATION: (29)
<223> OTHER INFORMATION: Xaa is lysine, alanine, glycine, or threonine, or is absent
<220> FEATURE:
<221> NAME/KEY: MISC_FEATURE
<222> LOCATION: (30)
<223> OTHER INFORMATION: Xaa is cysteine, or is absent

<400> SEQUENCE: 46

```
Xaa Xaa Gln Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Xaa Xaa
            20                  25                  30
```

<210> SEQ ID NO 47
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine

```
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (15)
<223> OTHER INFORMATION: Xaa is aspartic acid or cysteine
<220> FEATURE:
<221> NAME/KEY: MISC_FEATURE
<222> LOCATION: (16)
<223> OTHER INFORMATION: Xaa is glutamic acid or serine
<220> FEATURE:
<221> NAME/KEY: MISC_FEATURE
<222> LOCATION: (17)
<223> OTHER INFORMATION: Xaa is lysine or arginine
<220> FEATURE:
<221> NAME/KEY: MISC_FEATURE
<222> LOCATION: (20)
<223> OTHER INFORMATION: Xaa is glutamine or lysine
<220> FEATURE:
<221> NAME/KEY: MISC_FEATURE
<222> LOCATION: (21)
<223> OTHER INFORMATION: Xaa is aspartic acid or glutamic acid
<220> FEATURE:
<221> NAME/KEY: MISC_FEATURE
<222> LOCATION: (24)
<223> OTHER INFORMATION: Xaa is valine or glutamine
<220> FEATURE:
<221> NAME/KEY: MISC_FEATURE
<222> LOCATION: (30)
<223> OTHER INFORMATION: Xaa is cysteine or is absent

<400> SEQUENCE: 47

Tyr Xaa Gln Gly Thr Phe Xaa Ser Asp Xaa Ser Xaa Tyr Leu Xaa Xaa
1               5                   10                  15

Xaa Arg Ala Xaa Xaa Phe Val Xaa Trp Leu Met Asn Thr Xaa
            20                  25                  30


<210> SEQ ID NO 48
<211> LENGTH: 12
<212> TYPE: PRT
<213> ORGANISM: Homo sapiens

<400> SEQUENCE: 48

Glu Ser Lys Tyr Gly Pro Pro Cys Pro Ser Cys Pro
1               5                   10


<210> SEQ ID NO 49
<211> LENGTH: 3
<212> TYPE: PRT
<213> ORGANISM: Artificial Sequence
<220> FEATURE:
<223> OTHER INFORMATION: Variant of hinge region

<400> SEQUENCE: 49

Ser Cys Pro
1


<210> SEQ ID NO 50
<211> LENGTH: 4
<212> TYPE: PRT
<213> ORGANISM: Artificial Sequence
<220> FEATURE:
<223> OTHER INFORMATION: Variant of hinge region

<400> SEQUENCE: 50

Pro Ser Cys Pro
1
```

-continued

<210> SEQ ID NO 51
<211> LENGTH: 221
<212> TYPE: PRT
<213> ORGANISM: Homo sapiens

<400> SEQUENCE: 51

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

<210> SEQ ID NO 52
<211> LENGTH: 11
<212> TYPE: PRT
<213> ORGANISM: Artificial Sequence
<220> FEATURE:
<223> OTHER INFORMATION: Variant of hinge region

<400> SEQUENCE: 52

```
Glu Ser Lys Tyr Gly Pro Pro Pro Ser Cys Pro
1               5                   10
```

<210> SEQ ID NO 53
<211> LENGTH: 11
<212> TYPE: PRT
<213> ORGANISM: Artificial Sequence
<220> FEATURE:
<223> OTHER INFORMATION: Variant of hinge region

<400> SEQUENCE: 53

```
Glu Ser Lys Tyr Gly Pro Pro Cys Pro Ser Pro
1               5                   10
```

<210> SEQ ID NO 54
<211> LENGTH: 10
<212> TYPE: PRT

-continued

<213> ORGANISM: Artificial Sequence
<220> FEATURE:
<223> OTHER INFORMATION: Variant of hinge region

<400> SEQUENCE: 54

Glu Ser Lys Tyr Gly Pro Pro Cys Pro Ser
1 5 10

<210> SEQ ID NO 55
<211> LENGTH: 10
<212> TYPE: PRT
<213> ORGANISM: Artificial Sequence
<220> FEATURE:
<223> OTHER INFORMATION: Variant of hinge region

<400> SEQUENCE: 55

Glu Ser Lys Tyr Gly Pro Pro Cys Pro Pro
1 5 10

<210> SEQ ID NO 56
<211> LENGTH: 8
<212> TYPE: PRT
<213> ORGANISM: Artificial Sequence
<220> FEATURE:
<223> OTHER INFORMATION: Variant of hinge region

<400> SEQUENCE: 56

Lys Tyr Gly Pro Pro Cys Pro Ser
1 5

<210> SEQ ID NO 57
<211> LENGTH: 8
<212> TYPE: PRT
<213> ORGANISM: Artificial Sequence
<220> FEATURE:
<223> OTHER INFORMATION: Variant of hinge region

<400> SEQUENCE: 57

Glu Ser Lys Tyr Gly Pro Pro Cys
1 5

<210> SEQ ID NO 58
<211> LENGTH: 7
<212> TYPE: PRT
<213> ORGANISM: Artificial Sequence
<220> FEATURE:
<223> OTHER INFORMATION: Variant of hinge region

<400> SEQUENCE: 58

Glu Lys Tyr Gly Pro Pro Cys
1 5

<210> SEQ ID NO 59
<211> LENGTH: 6
<212> TYPE: PRT
<213> ORGANISM: Artificial Sequence
<220> FEATURE:
<223> OTHER INFORMATION: Variant of hinge region

<400> SEQUENCE: 59

Glu Ser Pro Ser Cys Pro
1 5

<210> SEQ ID NO 60
<211> LENGTH: 5
<212> TYPE: PRT
<213> ORGANISM: Artificial Sequence
<220> FEATURE:
<223> OTHER INFORMATION: Variant of hinge region

<400> SEQUENCE: 60

Glu Pro Ser Cys Pro
1 5

<210> SEQ ID NO 61
<211> LENGTH: 4
<212> TYPE: PRT
<213> ORGANISM: Artificial Sequence
<220> FEATURE:
<223> OTHER INFORMATION: Variant of hinge region

<400> SEQUENCE: 61

Pro Ser Cys Pro
1

<210> SEQ ID NO 62
<211> LENGTH: 10
<212> TYPE: PRT
<213> ORGANISM: Artificial Sequence
<220> FEATURE:
<223> OTHER INFORMATION: Variant of hinge region

<400> SEQUENCE: 62

Glu Ser Lys Tyr Gly Pro Pro Ser Cys Pro
1 5 10

<210> SEQ ID NO 63
<211> LENGTH: 9
<212> TYPE: PRT
<213> ORGANISM: Artificial Sequence
<220> FEATURE:
<223> OTHER INFORMATION: Variant of hinge region

<400> SEQUENCE: 63

Lys Tyr Gly Pro Pro Pro Ser Cys Pro
1 5

<210> SEQ ID NO 64
<211> LENGTH: 9
<212> TYPE: PRT
<213> ORGANISM: Artificial Sequence
<220> FEATURE:
<223> OTHER INFORMATION: Variant of hinge region

<400> SEQUENCE: 64

Glu Ser Lys Tyr Gly Pro Ser Cys Pro
1 5

<210> SEQ ID NO 65
<211> LENGTH: 8
<212> TYPE: PRT
<213> ORGANISM: Artificial Sequence
<220> FEATURE:
<223> OTHER INFORMATION: Variant of hinge region

<400> SEQUENCE: 65

Glu Ser Lys Tyr Gly Pro Pro Cys
1 5

<210> SEQ ID NO 66
<211> LENGTH: 7
<212> TYPE: PRT
<213> ORGANISM: Artificial Sequence
<220> FEATURE:

<223> OTHER INFORMATION: Variant of hinge region

<400> SEQUENCE: 66

Lys Tyr Gly Pro Pro Cys Pro
1 5

<210> SEQ ID NO 67
<211> LENGTH: 7
<212> TYPE: PRT
<213> ORGANISM: Artificial Sequence
<220> FEATURE:
<223> OTHER INFORMATION: Variant of hinge region

<400> SEQUENCE: 67

Glu Ser Lys Pro Ser Cys Pro
1 5

<210> SEQ ID NO 68
<211> LENGTH: 6
<212> TYPE: PRT
<213> ORGANISM: Artificial Sequence
<220> FEATURE:
<223> OTHER INFORMATION: Variant of hinge region

<400> SEQUENCE: 68

Glu Ser Pro Ser Cys Pro
1 5

<210> SEQ ID NO 69
<211> LENGTH: 4
<212> TYPE: PRT
<213> ORGANISM: Artificial Sequence
<220> FEATURE:
<223> OTHER INFORMATION: Variant of hinge region

<400> SEQUENCE: 69

Glu Pro Ser Cys
1

<210> SEQ ID NO 70
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one monomer
<220> FEATURE:
<221> NAME/KEY: MISC_FEATURE
<222> LOCATION: (222)..(442)
<223> OTHER INFORMATION: Amino acids at position 222 to 442 form one monomer
<220> FEATURE:
<221> NAME/KEY: DISULFID
<222> LOCATION: (3)..(224)
<223> OTHER INFORMATION: Amino acids at position 3 and position 224 form an inter-disulfide bond
<220> FEATURE:
<221> NAME/KEY: DISULFID
<222> LOCATION: (35)..(95)
<223> OTHER INFORMATION: Amino acids at position 35 and position 95 form an intra-chain disulfide bond
<220> FEATURE:
<221> NAME/KEY: DISULFID
<222> LOCATION: (141)..(199)

-continued

<223> OTHER INFORMATION: Amino acids at position 141 and position 199
      form an intra-chain disulfide bond
<220> FEATURE:
<221> NAME/KEY: DISULFID
<222> LOCATION: (256)..(316)
<223> OTHER INFORMATION: Amino acids at position 256 and position 316
      form an intra-chain disulfide bond
<220> FEATURE:
<221> NAME/KEY: DISULFID
<222> LOCATION: (362)..(420)
<223> OTHER INFORMATION: Amino acids at position 362 and position 420
      form an intra-chain disulfide bond

<400> SEQUENCE: 70

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
```

-continued

```
        340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

LIQUID FORMULATION OF LONG-ACTING CONJUGATE OF GLUCAGON DERIVATIVE

CROSS REFERENCE TO RELATED APPLICATIONS

This application is a National Stage of International Application No. PCT/KR2021/006441 filed May 24, 2021, claiming priority based on Korean Patent Application No. 10-2020-0061877 filed May 22, 2020.

INCORPORATION BY REFERENCE OF SEQUENCE LISTING

The content of the electronically submitted sequence listing, file name: Q269628_Sequence_Listing_As_Filed.txt; size: 37,782 bytes; and date of creation: Nov. 20, 2022, filed herewith, is incorporated herein by reference in its entirety.

TECHNICAL FIELD

The present invention relates to a liquid formulation of a long-acting conjugate of a glucagon derivative and a method for preparing the same.

BACKGROUND ART

Due to recent economic growth and changes in dietary habits, etc., the incidence of metabolic syndrome-associated diseases including various diseases such as obesity, hyperlipidemia, hypertension, arteriosclerosis, hyperinsulinemia, diabetes, or liver diseases is rapidly increasing. These diseases may occur independently, but in general, they mostly occur in close relationship with one another, being accompanied by various symptoms.

The World Health Organization (WHO) has reported that more than one billion adults are overweight worldwide, and among them, over three million are clinically diagnosed with obesity, and in particular, 250,000 people in Europe and more than 2.5 million people worldwide die of overweight- or obesity-related diseases every year.

Obesity is now recognized as a serious disease prevalent across the globe and is a cause of various diseases, but it is believed that it can be overcome by self-reliant efforts. However, obesity is not readily curable, because it is a complex disease associated with the mechanisms of appetite control and energy metabolism. Accordingly, the treatment of obesity requires not only the patient's own efforts, but also a method capable of treating abnormal mechanisms associated with appetite control and energy metabolism. Thus, efforts have been made to develop drugs for treating such abnormal mechanisms.

As a result of these efforts, anti-obesity drugs such as RIMONABANT® (SANOFI-AVENTIS), SIBUTRAMINE® (ABBOTT), CONTRAVE® (TAKEDA), ORLISTAT® (ROCHE), etc. have been developed, but they have the disadvantages of serious adverse effects or very weak anti-obesity effects. Accordingly, many extensive studies have been made to develop novel therapeutic agents for obesity which can resolve the problems of the conventional anti-obesity drugs. Recently, glucagon derivatives have received much attention.

Glucagon is produced by the pancreas when blood glucose levels drop as a result of other medications or diseases, or hormone or enzyme deficiencies. Glucagon stimulates glycogen breakdown in the liver, and facilitates glucose release to raise blood glucose levels to a normal range. Additionally, glucagon has been shown to be effective in treating hypoglycemia. The hypoglycemic therapeutic effect of glucagon is the result of stimulating the degradation of glycogen to glucose (glycogen breakdown) or increasing glucose production (glucose biosynthesis) derived from amino acid precursors resulting in increased glucose outflow from the liver.

In addition to the effect of increasing the blood glucose levels, glucagon suppresses appetite and activates hormone-sensitive lipase of adipocytes to facilitate lipolysis, thereby showing an anti-obesity effect. However, the use of glucagon as a therapeutic agent has been limited due to its low solubility and its property of being precipitated at neutral pH.

Accordingly, the glucagon with improved properties alone can be effectively used for the treatment of severe hypoglycemia, non-alcoholic steatohepatitis (NASH), dyslipidemia, etc. due to increase in fat decomposition and β-oxidation in the liver.

Drugs for the treatment of hypoglycemia include diazoxide, octreotide, glucagon, etc. Among these, glucagon is currently used as a lyophilized formulation due to its low solubility and precipitation at neutral pH, which is inconvenient because it needs to be dissolved in a solvent before use. Furthermore, when glucagon is used as a therapeutic agent for the treatment of congenital hyperinsulinism, which requires long-term treatment due to its short half-life, the use of glucagon has been limited due to frequent administration.

With this background, the present inventors have developed glucagon derivatives with partial modifications in the amino acid sequence of glucagon for the improvement of the therapeutic effects of glucagon on hypoglycemia and obesity by improving the physical properties of glucagon (International Publication Nos. WO 2016/108586 and WO 2017/003191). It was confirmed that the developed glucagon derivatives activate glucagon receptors through in vitro activity measurement. In addition, a long-acting conjugate of the glucagon derivatives that increases in vivo half-life has been developed, and it was confirmed that the long-acting conjugate could exhibit improved solubility and high stability at neutral pH due to altered pI, which is different from that of natural glucagon (International Publication No. WO 2017/003191).

DISCLOSURE

Technical Problem

There is a need for the development of a stable liquid formulation capable of storing a long-acting conjugate of a glucagon derivative for a long time without concern for virus contamination.

Technical Solution

It is one object of the present invention to provide a liquid formulation of a long-acting conjugate of a glucagon derivative.

It is another object of the present invention to provide a method for preparing the liquid formulation.

Advantageous Effects

The liquid formulation according to the present invention has an economic advantage of providing storage stability to the conjugate of the present invention having a large molecular weight in a simple formulation.

BRIEF DESCRIPTION OF DRAWINGS

FIGS. 1A and 1B show the results of confirming the stability of the long-acting conjugate of the glucagon derivative according to the type of buffering agents. Specifically, the compositions shown in Table 3 of Example 2 (compositions #1, #3, and #5 in Table 3) were used as liquid formulations of the long-acting conjugates of the glucagon derivatives, respectively, and stored at 25° C. for 7 weeks, and as a result, stability was measured. Among the results, sodium acetate and histidine formulations as buffers showed the highest stability for 7 weeks at 25° C.

DETAILED DESCRIPTION OF THE INVENTION

One aspect for implementing the present invention provides a liquid formulation of a long-acting conjugate of a glucagon derivative. The long-acting conjugate refers to a substance in which a peptide having activity for glucagon derivatives is covalently bonded to an immunoglobulin Fc fragment by a linker.

In one embodiment, the present invention relates to a liquid formulation of a long-acting conjugate of a glucagon derivative peptide, wherein the liquid formulation includes: a long-acting conjugate of a glucagon derivative peptide in a pharmacologically effective amount, in which a glucagon derivative peptide and an immunoglobulin Fc fragment are linked to each other; and an albumin-free stabilizer including i) a buffering agent, and ii) sugar alcohol, saccharide, or a combination thereof. The long-acting conjugate may refer to a substance in which a glucagon derivative peptide is covalently bonded to an immunoglobulin Fc fragment.

In one embodiment, the liquid formulation is a liquid formulation including the long-acting conjugate of Chemical Formula 1 below; a buffering agent; and sugar alcohol, saccharide, or a combination thereof:

[Chemical Formula 1]

$$X—L_a—F$$

In Chemical Formula 1 above,

X is a glucagon derivative peptide;

L is a linker;

a is 0 or a natural number, with the proviso that when a is 2 or more, each L is independent of each other;

F is an immunoglobulin Fc fragment; and

— represents a covalent bond:

[General Formula 1]

Y—X2-QGTF—X7-SD-X10-S—X12-X13-X14-X15-X16-X17-X18-X19-X20-X21-F—X23-X24-W-L-X27-X28-T-X30 (General Formula 1, SEQ ID NO: 46)

In General Formula 1 above,

X2 is α-methyl-glutamic acid, aminoisobutyric acid (Aib), D-alanine, glycine, Sar (N-methylglycine), serine, or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C), or is absent;

X17 is aspartic acid (D), glutamine (Q), glutamic acid (E), lysine (K), arginine (R), serine (S), cysteine (C), or valine (V), or is absent;

X18 is alanine (A), aspartic acid (D), glutamine (Q), glutamic acid (E), arginine (R), valine (V), or cysteine (C), or is absent;

X19 is alanine (A), arginine (R), serine (S), valine (V), or cysteine (C), or is absent;

X20 is lysine (K), histidine (H), glutamic acid (E), glutamine (Q), aspartic acid (D), arginine (R), α-methyl-glutamic acid, or cysteine (C), or is absent;

X21 is aspartic acid (D), glutamic acid (E), leucine (L), valine (V), or cysteine (C), or is absent;

X23 is isoleucine (I), valine (V), or arginine (R), or is absent;

X24 is valine (V), arginine (R), alanine (A), cysteine (C), glutamic acid (E), lysine (K), glutamine (Q), α-methyl-glutamic acid, or leucine (L), or is absent;

X27 is isoleucine (I), valine (V), alanine (A), lysine (K), methionine (M), glutamine (Q), or arginine (R), or is absent;

X28 is glutamine (Q), lysine (K), asparagine (N), or arginine (R), or is absent;

X30 is cysteine (C), or is absent (with the proviso that when the amino acid sequence of General Formula 1 is identical to SEQ ID NO: 1 and SEQ ID NO: 12, it is excluded).

The Aib refers to aminoisobutyric acid. In the present specification, the "Aib" may be used interchangeably with "2-aminoisobutyric acid" or "aminoisobutyric acid".

In the liquid formulation according to any one of the preceding embodiments, the glucagon derivative peptide in the long-acting conjugate of the glucagon derivative peptide is characterized in that it that includes the amino acid sequence of General Formula 2 below:

Y-Aib-QGTF—X7-SD-X10-S—X12-Y-L-X15-X16-X17-R-A-X20-X21-F—V—X24-W-L-M-N-T-X30 (General Formula 2, SEQ ID NO: 47)

In General Formula 2 above,

X7 is threonine (T), valine (V), or cysteine (C);

X10 is tyrosine (Y) or cysteine (C);

X12 is lysine (K) or cysteine (C);

X15 is aspartic acid (D) or cysteine (C);

X16 is glutamic acid (E) or serine (S);

X17 is lysine (K) or arginine (R);

X20 is glutamine (Q) or lysine (K);

X21 is aspartic acid (D) or glutamic acid (E);

X24 is valine (V) or glutamine (Q);

X30 is cysteine (C) or is absent (with the proviso that when the amino acid sequence of General Formula 2 is identical to SEQ ID NO: 1 and SEQ ID NO: 12, it is excluded).

In the liquid formulation according to any one of the preceding embodiments, the liquid formulation is characterized in that it is a liquid formulation of a long-acting conjugate, which includes: 18 nmol/mL to 936 nmol/mL of the long-acting conjugate of Chemical Formula 1; a buffering agent in an amount for maintaining the pH of the liquid formulation in the range of 4.8 to 6.5; and 1.0% (w/v) to 20% (w/v) of a sugar alcohol, a saccharide, or a combination thereof.

In the liquid formulation according to any one of the preceding embodiments, the liquid formulation is characterized in that it further includes one or more components selected from the group consisting of a saccharide, a sugar alcohol, a non-ionic surfactant and an amino acid.

In the liquid formulation according to any one of the preceding embodiments, the liquid formulation is characterized in that it is a liquid formulation of a long-acting conjugate of a glucagon derivative peptide further including a saccharide or a sugar alcohol, an amino acid, or both.

In the liquid formulation according to any one of the preceding embodiments, the liquid formulation is characterized in that it includes a buffering agent, a saccharide or a sugar alcohol, and an amino acid.

In the liquid formulation according to any one of the preceding embodiments, the liquid formulation is characterized in that it includes a buffering agent, a saccharide or a sugar alcohol, a non-ionic surfactant, an amino acid.

In the liquid formulation according to any one of the preceding embodiments, the liquid formulation is characterized in that it further includes a non-ionic surfactant, an amino acid, or both.

In the liquid formulation according to any one of the preceding embodiments, the liquid formulation is characterized in that it includes i) a saccharide or a sugar alcohol, ii) a non-ionic surfactant, or a combination thereof.

In the liquid formulation according to any one of the preceding embodiments, the glucagon derivative peptide is characterized in that it includes an amino acid sequence selected from the group consisting of SEQ ID NOS: 2 to 11 and 13 to 45.

The peptide may include an amino acid sequence selected from the group consisting of SEQ ID NOS: 2 to 11 and 13 to 45, and may consist (essentially) of an amino acid sequence of SEQ ID NOS: 2 to 11 and 13 to 45, but is not limited thereto.

Examples of such a peptide include, but are not particularly limited to, a peptide including or consisting (essentially) of an amino acid sequence selected from the group consisting of SEQ ID NOS: 13, 15 and 36 to 44. As another example, the peptide may be a peptide including or consisting (essentially) of an amino acid sequence selected from the group consisting of SEQ ID NO: 37, but is not particularly limited thereto.

In the liquid formulation according to any one of the preceding embodiments, the L is characterized in that it is polyethylene glycol.

In the liquid formulation according to any one of the preceding embodiments, the formula weight of the ethylene glycol repeating unit moiety in L is in the range of 1 kDa to 100 kDa.

In the liquid formulation according to any one of the preceding embodiments, the structure of Chemical Formula 1 above is characterized in that it is represented by the structure of Chemical Formula 2 below:

[Chemical Formula 2]

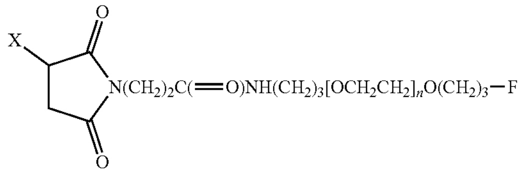

wherein, X and F are as defined in Chemical Formula 1.

In the liquid formulation according to any one of the preceding embodiments, the ethylene glycol repeating unit has a formula of $[OCH_2CH_2]_n$, wherein n is a natural number, and the average molecular weight of the $[OCH_2CH_2]_n$ region in the peptide, for example, the number average molecular weight is determined to be 1 kDa to 100 kDa.

In the liquid formulation according to any one of the preceding embodiments, the value of n is characterized in that it is determined such that the average molecular weight of the $[OCH_2CH_2]_n$ region in the peptide conjugate, for example, the number average molecular weight, is 10 kDa.

In the liquid formulation according to any one of the preceding embodiments, the X is characterized in that it is amidated at the C-terminus.

In the liquid formulation according to any one of the preceding embodiments, the X is characterized in that it is linked via a sulfur atom of cysteine in the peptide.

In the liquid formulation according to any one of the preceding embodiments, the immunoglobulin Fc fragment is characterized in that it is derived from IgG4.

In the liquid formulation according to any one of the preceding embodiments, the F is characterized in that it is a structure in which two polypeptide chains are linked by a disulfide bond, and are linked only through a nitrogen atom in one of the two chains.

In the liquid formulation according to any one of the preceding embodiments, the F is characterized in that it includes a monomer of the amino acid sequence of SEQ ID NO: 51.

In the liquid formulation according to any one of the preceding embodiments, the F is characterized in that it is a homodimer of the monomers of the amino acid sequence of SEQ ID NO: 51.

In the liquid formulation according to any one of the preceding embodiments, the F is characterized in that it is linked through a nitrogen atom of proline at the N-terminus thereof.

In the liquid formulation according to any one of the preceding embodiments, the immunoglobulin Fc fragment and X are characterized in that it is non-glycosylated.

In the liquid formulation according to the preceding embodiments, the liquid formulation is characterized in that it does not further include one or more components selected from the group consisting of a non-ionic surfactant and an amino acid.

In the liquid formulation according to any one of the preceding embodiments, the buffering agent is characterized in that it is selected from the group consisting of citric acid and a salt thereof, acetic acid and a salt thereof, histidine and a salt thereof, phosphoric acid and a salt thereof, and a combination thereof.

In the liquid formulation according to any one of the preceding embodiments, the buffering agent is characterized in that it is acetic acid and a salt thereof.

In the liquid formulation according to any one of the preceding embodiments, the pH of the liquid formulation is characterized in that it is 4.8 to 6.5.

In the liquid formulation according to any one of the preceding embodiments, the pH of the liquid formulation is characterized in that it is 4.8 to 6.0.

In the liquid formulation according to any one of the preceding embodiments, the pH of the liquid formulation is characterized in that it is 4.8 to 5.5.

In the liquid formulation according to any one of the preceding embodiments, the concentration of the buffering agent is characterized in that it is 5 mM to 100 mM for maintaining the pH of the liquid formulation in the range of 4.8 to 6.5.

In the liquid formulation according to any one of the preceding embodiments, the saccharide or sugar alcohol is characterized in that it is one or more selected from the group consisting of sucrose, mannitol and sorbitol.

In the liquid formulation according to any one of the preceding embodiments, the saccharide or sugar alcohol is characterized in that it is present in a concentration of 1% (w/v) to 20% (w/v) in the liquid formulation.

In the liquid formulation according to any one of the preceding embodiments, the long-acting conjugate is characterized in that it is present in a concentration of 18 nmol/mL to 2,807 nmol/mL, 18 nmol/mL to 936 nmol/mL, 90 nmol/mL to 562 nmol/mL, 187 nmol/mL to 562 nmol/mL, 187 nmol/mL to 2,807 nmol/mL, or 93 nmol/mL to 936 nmol/mL in the liquid formulation.

In the liquid formulation according to any one of the preceding embodiments, the saccharide is characterized in that it is glucose, fructose, galactose, lactose, maltose, sucrose, or a combination thereof.

In the liquid formulation according to any one of the preceding embodiments, the saccharide is characterized in that it is sucrose.

In the liquid formulation according to any one of the preceding embodiments, the saccharide is characterized in that it is present in a concentration of 3% (w/v) to 15% (w/v)

In the liquid formulation according to any one of the preceding embodiments, the sugar alcohol is characterized in that it is one or more selected from the group consisting of mannitol and sorbitol.

In the liquid formulation according to any one of the preceding embodiments, the liquid formulation is characterized in that it further includes one or more components selected from the group consisting of a non-ionic surfactant and an amino acid.

In the liquid formulation according to the preceding embodiments, the liquid formulation is characterized in that it does not include an isotonic agent.

In the liquid formulation according to any one of the preceding embodiments, the non-ionic surfactant is characterized in that it is poloxamer, polysorbate, or a combination thereof.

In the liquid formulation according to any one of the preceding embodiments, the non-ionic surfactant is characterized in that it is selected from the group consisting of poloxamer 188, polysorbate 20, polysorbate 40, polysorbate 60, polysorbate 80, and a combination thereof.

In the liquid formulation according to any one of the preceding embodiments, the non-ionic surfactant is characterized in that it is present in a concentration of 0.001% (w/v) to 0.5% (w/v) in the liquid formulation.

In the liquid formulation according to any one of the preceding embodiments, the amino acid is characterized in that it is selected from the group consisting of methionine, arginine, histidine, glycine, cysteine, lysine, and a combination thereof.

In the liquid formulation according to any one of the preceding embodiments, the amino acid is characterized in that it is present in a concentration of 0.01 mg/mL to 1 mg/mL in the liquid formulation.

In the liquid formulation according to any one of the preceding embodiments, the liquid formulation is characterized in that it includes: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 6.5; 1% (w/v) to 20% (w/v) of a sugar alcohol, a saccharide, or a combination thereof; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

In the liquid formulation according to any one of the preceding embodiments, the liquid formulation is characterized in that it includes: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 6.5; 4% (w/v) to 10% (w/v) of a sugar alcohol, a saccharide, or a combination thereof; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

In the liquid formulation according to any one of the preceding embodiments, the liquid formulation is characterized in that it includes: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 6.0; 4% (w/v) to 10% (w/v) of a sugar alcohol, a saccharide, or a combination thereof; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

In the liquid formulation according to any one of the preceding embodiments, the liquid formulation is characterized in that it includes: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 4% (w/v) to 10% (w/v) of a sugar alcohol, a saccharide, or a combination thereof; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

In the liquid formulation according to any one of the preceding embodiments, the liquid formulation is characterized in that it includes a buffering agent in the range of pH 4.8 to 6.5; a saccharide or a sugar alcohol selected from the group consisting of sucrose, mannitol, sorbitol, and a combination thereof; an amino acid selected from the group consisting of methionine, arginine, histidine, glycine, cysteine, lysine, and a combination thereof; and polysorbate as a non-ionic surfactant.

In the liquid formulation according to any one of the preceding embodiments, the glucagon derivative peptide in the long-acting conjugate of the glucagon derivative peptide is characterized in that it includes the amino acid sequence of General Formula 1 below:

Y—X2-QGTF—X7-SD-X10-S—X12-X13-X14-X15-X16-X17-X18-X19-X20-X21-F—X23-X24-W-L-X27-X28-T-X30 (General Formula 1, SEQ ID NO: 46)

In General Formula 1 above,

X2 is α-methyl-glutamic acid, aminoisobutyric acid (Aib), D-alanine, glycine, Sar (N-methylglycine), serine, or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C), or is absent;

X17 is aspartic acid (D), glutamine (Q), glutamic acid (E), lysine (K), arginine (R), serine (S), cysteine (C), or valine (V), or is absent;

X18 is alanine (A), aspartic acid (D), glutamine (Q), glutamic acid (E), arginine (R), valine (V), or cysteine (C), or is absent;

X19 is alanine (A), arginine (R), serine (S), valine (V), or cysteine (C), or is absent;

X20 is lysine (K), histidine (H), glutamic acid (E), glutamine (Q), aspartic acid (D), arginine (R), α-methyl-glutamic acid, or cysteine (C), or is absent;

X21 is aspartic acid (D), glutamic acid (E), leucine (L), valine (V), or cysteine (C), or is absent;

X23 is isoleucine (I), valine (V), or arginine (R), or is absent;

X24 is valine (V), arginine (R), alanine (A), cysteine (C), glutamic acid (E), lysine (K), glutamine (Q), α-methyl-glutamic acid, or leucine (L), or is absent;

X27 is isoleucine (I), valine (V), alanine (A), lysine (K), methionine (M), glutamine (Q), or arginine (R), or is absent;

X28 is glutamine (Q), lysine (K), asparagine (N), or arginine (R), or is absent;

X30 is cysteine (C), or is absent (with the proviso that when the amino acid sequence of General Formula 1 is identical to SEQ ID NO: 1 and SEQ ID NO: 12, it is excluded).

In the liquid formulation according to any one of the preceding embodiments, in the General Formula 1 above, X2 is serine (S) or aminoisobutyric acid (Aib);

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D) or cysteine (C);

X16 is glutamic acid (E), serine (S), or cysteine (C);

X17 is aspartic acid (D), glutamic acid (E), lysine (K), arginine (R), serine (S), cysteine (C), or valine (V);

X18 is aspartic acid (D), glutamic acid (E), arginine (R), or cysteine (C);

X19 is alanine (A) or cysteine (C);

X20 is glutamine (Q), aspartic acid (D), lysine (K), or cysteine (C);

X21 is aspartic acid (D), glutamic acid (E), leucine (L), valine (V), or cysteine (C);

X23 is isoleucine (I), valine (V), or arginine (R);

X24 is valine (V), arginine (R), alanine (A), glutamic acid (E), lysine (K), glutamine (Q), or leucine (L);

X27 is isoleucine (I), valine (V), alanine (A), methionine (M), glutamine (Q), or arginine (R);

X28 is glutamine (Q), lysine (K), asparagine (N), or arginine (R);

X30 is cysteine (C), or is absent (with the proviso that when the amino acid sequence of General Formula 1 is identical to SEQ ID NO: 1 and SEQ ID NO: 12, it is excluded).

In the liquid formulation according to any one of the preceding embodiments, in the General Formula 1 above, X2 is serine (S) or aminoisobutyric acid (Aib);

X7 is cystine (C), threonine (T), or valine (V);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D) or cysteine (C);

X16 is glutamic acid (E), serine (S), or cysteine (C);

X17 is glutamic acid (E), lysine (K), arginine (R), cysteine (C), or valine (V);

X18 is arginine (R) or cysteine (C);

X19 is alanine (A) or cysteine (C);

X20 is glutamine (Q) or lysine (K);

X21 is aspartic acid (D), glutamic acid (E), valine (V), or cysteine (C);

X23 is valine (V);

X24 is valine (V) or glutamine (Q);

X27 is methionine (M);

X28 is asparagine (N) or arginine (R);

X30 is cysteine (C), or is absent (with the proviso that when the amino acid sequence of General Formula 1 is identical to SEQ ID NO: 1 and SEQ ID NO: 12, it is excluded).

In the liquid formulation according to any one of the preceding embodiments, in the General Formula 1 above, X2 is aminoisobutyric acid (Aib);

X7 is cystine (C), threonine (T), or valine (V);

X10 is tyrosine (Y) or cysteine (C);

X12 is lysine (K);

X13 is tyrosine (Y) or cysteine (C);

X14 is leucine (L) or cysteine (C);

X15 is aspartic acid (D) or cysteine (C);

X16 is glutamic acid (E), serine (S), or cysteine (C);

X17 is lysine (K), arginine (R), cysteine (C), or valine (V);

X18 is arginine (R) or cysteine (C);

X19 is alanine (A) or cysteine (C);

X20 is glutamine (Q) or lysine (K);

X21 is aspartic acid (D), glutamic acid (E), or cysteine (C);

X23 is valine (V);

X24 is glutamine (Q);

X27 is methionine (M);

X28 is asparagine (N) or arginine (R);

X30 is cysteine (C), or is absent (with the proviso that when the amino acid sequence of General Formula 1 is identical to SEQ ID NO: 1 and SEQ ID NO: 12, it is excluded).

In the liquid formulation according to any one of the preceding embodiments, in the General Formula 1 above, X2 is serine (S) or aminoisobutyric acid (Aib);

X7 is cystine (C), threonine (T), or valine (V);

X10 is tyrosine (Y) or cysteine (C);

X12 is lysine (K) or cysteine (C);

X13 is tyrosine (Y) or cysteine (C);

X14 is leucine (L) or cysteine (C);
X15 is aspartic acid (D) or cysteine (C);
X16 is glutamic acid (E), serine (S), or cysteine (C);
X17 is aspartic acid (D), glutamic acid (E), lysine (K), arginine (R), serine (S), cysteine (C), or valine (V);
X18 is aspartic acid (D), glutamic acid (E), arginine (R), or cysteine (C);
X19 is alanine (A) or cysteine (C);
X20 is glutamine (Q), aspartic acid (D), or lysine (K);
X21 is aspartic acid (D) or glutamic acid (E);
X23 is valine (V);
X24 is valine (V) or glutamine (Q);
X27 is isoleucine (I) or methionine (M);
X28 is asparagine (N) or arginine (R);
X30 is cysteine (C), or is absent (with the proviso that when the amino acid sequence of General Formula 1 is identical to SEQ ID NO: 1 and SEQ ID NO: 12, it is excluded).

In the liquid formulation according to any one of the preceding embodiments, in the General Formula 1 above,
X2 is aminoisobutyric acid (Aib);
X7 is threonine (T);
X10 is tyrosine (Y);
X12 is lysine (K);
X13 is tyrosine (Y);
X14 is leucine (L);
X15 is aspartic acid (D) or cysteine (C);
X16 is glutamic acid (E), serine (S), or cysteine (C);
X17 is lysine (K) or arginine (R);
X18 is arginine (R);
X19 is alanine (A);
X20 is glutamine (Q), cystine (C), or lysine (K);
X21 is aspartic acid (D), cysteine (C), valine (V), or glutamic acid (E);
X23 is valine (V) or arginine (R);
X24 is glutamine (Q) or leucine (L);
X27 is methionine (M);
X28 is asparagine (N) or arginine (R);
X30 is absent (with the proviso that when the amino acid sequence of General Formula 1 is identical to SEQ ID NO: 1 and SEQ ID NO: 12, it is excluded).

In the liquid formulation according to any one of the preceding embodiments, the glucagon derivative peptide in the long-acting conjugate of the glucagon derivative peptide is characterized in that it includes the amino acid sequence of General Formula 2 below:

Y-Aib-QGTF—X7-SD-X10-S—X12-Y-L-X15-X16-X17-R-A-X20-X21-F—V—X24-W-L-M-N-T-X30 (General Formula 2, SEQ ID NO: 47)

In General Formula 2 above,
X7 is threonine (T), valine (V), or cysteine (C);
X10 is tyrosine (Y) or cysteine (C);
X12 is lysine (K) or cysteine (C);
X15 is aspartic acid (D) or cysteine (C);
X16 is glutamic acid (E) or serine (S);
X17 is lysine (K) or arginine (R);
X20 is glutamine (Q) or lysine (K);
X21 is aspartic acid (D) or glutamic acid (E);
X24 is valine (V) or glutamine (Q);
X30 is cysteine (C) or is absent (with the proviso that when the amino acid sequence of General Formula 2 is identical to SEQ ID NO: 1 and SEQ ID NO: 12, it is excluded).

In the liquid formulation according to any one of the preceding embodiments, the glucagon derivative peptide is characterized in that it includes an amino acid sequence selected from SEQ ID NOS: 2 to 45.

In the liquid formulation according to any one of the preceding embodiments, the glucagon derivative peptide is characterized in that it includes an amino acid sequence selected from SEQ ID NOS: 13, 15, and 36 to 44.

In the liquid formulation according to any one of the preceding embodiments, the glucagon derivative peptide is characterized in that it includes an amino acid sequence selected from SEQ ID NO: 37.

In the liquid formulation according to any one of the preceding embodiments, the glucagon derivative peptide is characterized in that it has a pI different from that of native glucagon, a pI of 6.8, for example, a pI of 6.5 or less or 7.0 or more.

In the liquid formulation according to any one of the preceding embodiments, the glucagon derivative peptide is characterized in that it has a carboxyl group (COOH) at the C-terminus thereof.

In the liquid formulation according to any one of the preceding embodiments, the glucagon derivative peptide is characterized in that it is a derivative of native glucagon capable of activating a glucagon receptor.

In the liquid formulation according to any one of the preceding embodiments, the pI of the glucagon derivative peptide is characterized in that it is 6 to 7, and the relative in vitro activity compared to the native glucagon is 200% or more in the long-acting conjugate of the glucagon derivative peptide.

In the liquid formulation according to any one of the preceding embodiments, each of the amino acids of at least one amino acid pair of the amino acid pairs of X10 and X14, X12 and X16, X16 and X20, X17 and X21, X20 and X24, and X24 and X28 of General Formula 1 or 2 above is characterized in that it is substituted with glutamic acid or lysine capable of forming a ring.

In the liquid formulation according to any one of the preceding embodiments, each of the amino acids of the amino acid pair of X12 and X16, the amino acid pair of X16 and X20, or the amino acid pair of X17 and X21 of General Formula 1 or 2 is characterized in that it is substituted with glutamic acid or lysine capable of forming a ring.

In the liquid formulation according to any one of the preceding embodiments, at least one amino acid pair of the amino acid pairs of X10 and X14, X12 and X16, X16 and X20, X17 and X21, X20 and X24, and X24 and X28 in General Formula 1 or 2 is characterized in that it forms a ring between each amino acid.

In the liquid formulation according to any one of the preceding embodiments, the ring is characterized in that it is a lactam ring.

In the liquid formulation according to any one of the preceding embodiments, X16 is characterized in that it is glutamic acid, X20 is lysine, and the side chains of X16 and X20 form a lactam ring in General Formula 1 or 2.

In the liquid formulation according to any one of the preceding embodiments, the immunoglobulin Fc region is characterized in that it is an IgG-, IgA-, IgD-, IgE-, or IgM-derived Fc fragment.

In the liquid formulation according to any one of the preceding embodiments, the immunoglobulin Fc region is characterized in that it is selected from the group consisting of (a) CH1 domain, CH2 domain, CH3 domain, and CH4 domain; (b) CH1 domain and CH2 domain; (c) CH1 domain and CH3 domain; (d) CH2 domain and CH3 domain; (e) a combination between one or two or more domains among CH1 domain, CH2 domain, CH3 domain and CH4 domain, and an immunoglobulin hinge region or a part of the hinge region; and (f) a dimer between each domain of the heavy chain constant region and the light chain constant region.

In the liquid formulation according to any one of the preceding embodiments, each domain of the immunoglobulin Fc fragment is characterized in that it is a hybrid of domains having different origins derived from an immunoglobulin selected from the group consisting of IgG, IgA, IgD, IgE, and IgM.

In the liquid formulation according to any one of the preceding embodiments, the immunoglobulin Fc fragment is characterized in that it is in the form of a dimer or multimer, composed of single-chain immunoglobulins consisting of domains of the same origin.

In the liquid formulation according to any one of the preceding embodiments, the immunoglobulin Fc fragment is characterized in that it is an IgG4 Fc fragment.

In the liquid formulation according to any one of the preceding embodiments, the immunoglobulin Fc fragment is characterized in that it is a human aglycosylated IgG4 Fc fragment.

In the liquid formulation according to any one of the preceding embodiments, the immunoglobulin Fc fragment is characterized in that it is a native Fc derivative, including: a modification where the site capable of forming an inter-disulfide bond is removed; a modification where several N-terminal amino acids from native Fc are removed; a modification where a methionine residue is added to the N-terminus of native Fc; a modification where complement binding sites are removed; a modification where antibody-dependent cell-mediated cytotoxicity (ADCC) sites are removed, or a combination thereof.

Another aspect for implementing the present invention provides a method for preparing the liquid formulation.

In one embodiment, the present invention relates to a method for preparing a liquid formulation, including: mixing (i) a long-acting conjugate of a glucagon derivative peptide, in which a glucagon derivative peptide and an immunoglobulin Fc fragment are linked to each other, with (ii) (a) a buffering agent and (b) sugar alcohol, saccharide or a combination thereof.

In the method according to the preceding embodiment, the stabilizer is characterized in that it further includes one or more components selected from the group consisting of a saccharide, a sugar alcohol, a non-ionic surfactant and an amino acid.

In the method according to any one of the preceding embodiments, the liquid formulation is characterized in that it is a liquid formulation of a long-acting conjugate of a glucagon derivative peptide further including a saccharide or a sugar alcohol, an amino acid, or both.

In the method according to any one of the preceding embodiments, the liquid formulation is characterized in that it includes a buffering agent, a saccharide or a sugar alcohol, and an amino acid.

In the method according to any one of the preceding embodiments, the liquid formulation is characterized in that it includes a buffering agent, a saccharide or a sugar alcohol, a non-ionic surfactant, and an amino acid.

MODE FOR CARRYING OUT THE INVENTION

Hereinafter, the present invention will be described in more detail.

Meanwhile, each of the explanations and exemplary embodiments disclosed herein can be applied to each other explanation and exemplary embodiment. That is, all of the combinations of various factors disclosed herein belong to the scope of the present invention. Moreover, the scope of the present invention should not be limited by the specific disclosure provided hereinbelow.

Additionally, those of ordinary skill in the art may be able to recognize or confirm, using only conventional experimentation, many equivalents to the particular aspects of the invention described herein. Furthermore, it is also intended that these equivalents be included in the present invention.

Throughout the entire specification of the present invention, not only the conventional one-letter and three-letter codes for naturally occurring amino acids, but also those three-letter codes generally allowed for other amino acids, such as α-aminoisobutyric acid (Aib), Sar (N-methylglycine), and α-methyl-glutamic acid, etc. are used. Additionally, the amino acids mentioned herein are abbreviated according to the nomenclature rules of IUPAC-IUB as follows:

alanine Ala, A
arginine Arg, R
asparagine Asn, N
aspartic acid Asp, D
cysteine Cys, C
glutamic acid Glu, E
glutamine Gln, Q
glycine Gly, G
histidine His, H
isoleucine Ile, I
leucine Leu, L
lysine Lys, K
methionine Met, M
phenylalanine Phe, F
proline Pro, P
serine Ser, S
threonine Thr, T
tryptophan Trp, W
tyrosine Tyr, Y
valine Val, V One aspect for implementing the present invention provides a liquid formulation of a long-acting conjugate of a glucagon derivative.

Specifically, the present invention relates to a liquid formulation of a long-acting conjugate of a glucagon derivative, including a long-acting conjugate of a glucagon derivative peptide in a pharmacologically effective amount, in which a glucagon derivative peptide and an immunoglobulin Fc fragment are linked to each other; and a buffering agent, and sugar alcohol, saccharide, or a combination thereof.

Specifically, the present invention provides a liquid formulation, including a long-acting conjugate of Chemical Formula 1 below; a buffering agent; and sugar alcohol, saccharide, or a combination thereof.

$$X—L_a—F$$

In Chemical Formula 1 above,

X is a glucagon derivative peptide;

L is a linker;

a is 0 or a natural number, with the proviso that when a is 2 or more, each L is independent of each other;

F is an immunoglobulin Fc fragment; and

— represents a covalent bond:

[General Formula 1]

Y—X2-QGTF—X7-SD-X10-S—X12-X13-X14-X15-X16-X17-X18-X19-X20-X21-F—X23-X24-W-L-X27-X28-T-X30 (General Formula 1, SEQ ID NO: 46)

In General Formula 1 above,

X2 is α-methyl-glutamic acid, aminoisobutyric acid (Aib), D-alanine, glycine, Sar (N-methylglycine), serine, or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C), or is absent;

X17 is aspartic acid (D), glutamine (Q), glutamic acid (E), lysine (K), arginine (R), serine (S), cysteine (C), or valine (V), or is absent;

X18 is alanine (A), aspartic acid (D), glutamine (Q), glutamic acid (E), arginine (R), valine (V), or cysteine (C), or is absent;

X19 is alanine (A), arginine (R), serine (S), valine (V), or cysteine (C), or is absent;

X20 is lysine (K), histidine (H), glutamic acid (E), glutamine (Q), aspartic acid (D), arginine (R), α-methyl-glutamic acid, or cysteine (C), or is absent;

X21 is aspartic acid (D), glutamic acid (E), leucine (L), valine (V), or cysteine (C), or is absent;

X23 is isoleucine (I), valine (V), or arginine (R), or is absent;

X24 is valine (V), arginine (R), alanine (A), cysteine (C), glutamic acid (E), lysine (K), glutamine (Q), α-methyl-glutamic acid, or leucine (L), or is absent;

X27 is isoleucine (I), valine (V), alanine (A), lysine (K), methionine (M), glutamine (Q), or arginine (R), or is absent;

X28 is glutamine (Q), lysine (K), asparagine (N), or arginine (R), or is absent;

X30 is cysteine (C), or is absent (with the proviso that when the amino acid sequence of General Formula 1 is identical to SEQ ID NO: 1 and SEQ ID NO: 12, it is excluded).

As used herein, the term "liquid formulation" refers to a drug formulated into a liquid form and is intended to include all liquid formulations for internal use and formulations for external use.

The liquid formulation of the present invention includes a long-acting conjugate of Chemical Formula 1 showing a pharmacological effect, and a substance capable of stably maintaining and/or storing the conjugate showing the pharmacological effect for a certain period of time when it is formulated in a liquid form. Components included in addition to the long-acting conjugate of Chemical Formula 1 that exhibit the pharmacological effect of the liquid formulation may be mixed with a stabilizer.

In the liquid formulation of the long-acting conjugate of Chemical Formula 1 of the present invention, storage stability is important for ensuring accurate dosage.

It was confirmed that the long-acting conjugate of Chemical Formula 1 is stable even when stored for a long time by including a specific concentration of the long-acting conjugate of Chemical Formula 1, which is a substance exhibiting a pharmacological effect; an amount of buffering agent to maintain the pH in the range of 4.8 to 6.5; and 1.0% (w/v) to 20% (w/v) of a sugar alcohol, a saccharide, or a combination thereof, thereby providing a novel formulation of the present invention.

The concentration of the long-acting conjugate of the glucagon derivative peptide included in the liquid formulation of the present invention may be about 18 nmol/mL to about 2,810 nmol/mL, about 18 nmol/mL to about 2,807 nmol/mL, about 18 nmol/mL to about 2,623 nmol/mL, about 18 nmol/mL to about 2,436 nmol/mL, about 18 nmol/mL to about 2,248 nmol/mL, about 18 nmol/mL to about 2,061 nmol/mL, about 18 nmol/mL to about 1,874 nmol/mL, about 18 nmol/mL to about 1,686 nmol/mL, about 18 nmol/mL to about 1,499 nmol/mL, about 18 nmol/mL to about 1,312 nmol/mL, about 18 nmol/mL to about 1,124 nmol/mL, about 18 nmol/mL to about 940 nmol/mL, about 18 nmol/mL to about 936 nmol/mL, about 18 nmol/mL to about 843 nmol/mL, about 18 nmol/mL to about 750 nmol/mL, about 18 nmol/mL to about 656 nmol/mL, about 18 nmol/mL to about 570 nmol/mL, about 18 nmol/mL to about 562 nmol/mL, about 18 nmol/mL to about 469 nmol/mL, about 18 nmol/mL to about 375 nmol/mL, about 18 nmol/mL to about 281 nmol/mL, about 18 nmol/mL to about 188 nmol/mL, about 18 nmol/mL to about 94 nmol/mL, about 187 nmol/mL, about 188 nmol/mL, about 187.09 nmol/mL, about 187.1 nmol/mL, about 93 nmol/mL to about 188 nmol/mL, about 93 nmol/mL to about 281 nmol/mL, about 93 nmol/mL to about 375 nmol/mL, about 93 nmol/mL to about 469 nmol/mL, about 93 nmol/mL to about 562 nmol/mL, about 93 nmol/mL to about 656 nmol/mL, about 93 nmol/mL to about 750 nmol/mL, about 93 nmol/mL to about 843 nmol/mL, about 93 nmol/mL to about 940 nmol/mL, about 93 nmol/mL to about 936 nmol/mL, about 187 nmol/mL to about 281 nmol/mL, about 187 nmol/mL to about 375 nmol/mL, about 187 nmol/mL to about 469 nmol/mL, about 187 nmol/mL to about 570 nmol/mL, or about 187 nmol/mL to about 562 nmol/mL, but is not limited thereto. In one embodiment, the concentration of the long-acting conjugate may be 18 nmol/mL to 936 nmol/mL, but is not limited thereto. As used herein, the term "stabilizer" refers to a substance that stably maintains components such as active ingredients for a specific period of time in a formulation.

The stabilizer of the present invention preferably contains no albumin. Human serum albumin that can be used as a protein stabilizer is prepared from human blood, and thus can be contaminated with human pathogenic virus, and gelatin or bovine serum albumin can cause diseases or can cause allergic reactions in some patients. The albumin-free stabilizer of the present invention does not contain a foreign protein such as human or animal serum albumin or purified gelatin, and thus is not susceptible to viral infection.

In the present invention, the stabilizer particularly refers to a substance that allows the long-acting conjugate of the glucagon derivative to be stored stably. In the long-acting conjugate of the glucagon derivative, the storage stability is not only important to ensure an accurate dosage, but also to inhibit potential generation of antigenic substances against the glucagon derivative.

The buffering agent, which is one component included in the liquid formulation of the present invention, can maintain the pH of a solution so that the pH of the liquid formulation does not rapidly change so as to make the long-acting conjugate of Chemical Formula 1 stable. The buffering agent may also be referred to as a buffer system, and the buffering agent or buffer system serves to maintain the pH of the liquid formulation. Any buffering agent capable of maintaining a pH that can stabilize the long-acting conjugate of Chemical Formula 1, which is the target material for stabilization, may be used without limitation.

The buffering agent may be a pH buffer, including phosphoric acid and its conjugate base (i.e., alkali salt such as phosphate: sodium phosphate, potassium phosphate, or a hydrogen or dihydrogen salt thereof), citric acid and a salt thereof (e.g., sodium citrate), acetic acid and a salt thereof (e.g., sodium acetate), or histidine and a salt thereof, and a mixture of these buffers may also be used, but the buffering agent is not limited thereto.

The liquid formulation of the present invention may include a buffer solution containing the buffering agent as a solvent of the liquid formulation, specifically, the buffer solution may be selected from the group consisting of a citrate buffer solution (e.g., a sodium citrate buffer solution), an acetate buffer solution (e.g., a sodium acetate buffer solution), a phosphate buffer solution (e.g., a sodium phosphate buffer solution), a histidine buffer solution, and a combination thereof. Additionally, the buffer solution or the buffering agent in the liquid formulation (citric acid and a salt thereof, acetic acid and a salt thereof, histidine and a salt thereof, phosphoric acid and a salt thereof, or a combination thereof) may be contained in a concentration sufficient to maintain a target pH of the liquid formulation.

The pH of the liquid formulation may be about 4.6 to about 6.5, for example, about 4.8 to about 6.5, about 4.8 to about 6.4, about 4.8 to about 6.3, about 4.8 to about 6.2, about 4.8 to about 6.1, about 4.8 to about 6.0, about 4.8 to about 5.9, about 4.8 to about 5.8, about 4.8 to 5.7, about 4.8 to about 5.6, about 4.8 to 5.5, about 4.8 to about 5.4, about 4.8 to about 5.3, about 4.8 to about 5.2, about 4.8 to about 5.1, about 4.9 to about 6.5, about 4.9 to about 6.4, about 4.9 to about 6.3, about 4.9 to about 6.2, about 4.9 to about 6.1, about 4.9 to about 6.0, about 4.9 to about 5.9, about 4.9 to about 5.8, about 4.9 to 5.7, about 4.9 to about 5.6, about 4.9 to 5.5, about 4.9 to about 5.4, about 4.9 to about 5.3, about 4.9 to about 5.2, about 4.9 to about 5.1, or about 5.0, 5.1, 5.2, 5.3, 5.4, 5.5, 5.6, 5.7, 5.8, 5.9, 6.0, 6.1, 6.2, 6.3, 6.4, or 6.5, but is not particularly limited thereto.

The concentration of the liquid formulation to reach the target pH may be about 1 mM to about 200 mM, more specifically, about 5 mM to about 100 mM, about 5 mM to about 80 mM, about 5 mM to about 40 mM, about 8 mM to about 40 mM, about 5 mM to about 30 mM, or about 5 mM to about 25 mM, about 10 mM to about 25 mM, about 15 mM to about 25 mM, about 18 mM to about 24 mM, about 18 mM to about 22 mM, or about 20 mM, but is not particularly limited thereto.

In one embodiment, the buffering agent may be acetic acid and a salt thereof, but is not limited thereto.

In another embodiment, the buffer solution may be an acetate buffer solution (e.g., sodium acetate buffer solution) or a citrate buffer solution (e.g., sodium citrate buffer solution), but is not particularly limited thereto.

Meanwhile, in the preparation of the liquid formulation, the components are dissolved in water (e.g., WFI), and the pH of the buffer solution or formulation can be adjusted to a desired pH using HCl and/or NaOH, etc., which is a method already commonly used in the art. Therefore, even if the pH adjuster is not additionally mentioned in the claims, it will be understood by those skilled in the art that the formulation can have an adjusted pH through such a method.

The sugar alcohol, which is one component included in the stabilizer of the present invention, refers to a substance containing a plurality of hydroxyl groups, and may include a substance, in which an aldehyde group and/or a ketone group of a saccharide is substituted with an alcohol group, and saccharides containing multiple hydroxyl groups. The saccharide or sugar alcohol may increase the stability of the long-acting conjugate of the glucagon derivative. For example, the sugar alcohol may be one or more selected from the group consisting of mannitol and sorbitol, but is not limited thereto.

The saccharide, which is one component included in the liquid formulation of the present invention, refers to monosaccharides, disaccharides, polysaccharides, oligosaccharides, etc., and can increase the stability of the long-acting conjugate of the glucagon derivative peptide. Specific examples may include monosaccharides such as mannose, glucose, fructose, galactose, fucose, and xylose; disaccharides such as lactose, maltose, and sucrose; and polysaccharides such as raffinose and dextran, but are not limited thereto.

In one embodiment, the saccharide may be glucose, fructose, galactose, lactose, maltose, sucrose, or a combination thereof, but is not limited thereto.

For example, the saccharide may be sucrose, but is not particularly limited thereto.

The sugar alcohol, saccharide, or a combination thereof may be present in a concentration of about 0.5% (w/v) to about 20% (w/v), about 0.5% (w/v) to about 15% (w/v), about 0.5% (w/v) to about 10% (w/v), about 0.5% (w/v) to about 8% (w/v), about 1% (w/v) to about 20% (w/v), about 1% (w/v) to 15% (w/v), about 1% (w/v) to 10% (w/v), about 1% (w/v) to 8% (w/v), about 2% (w/v) to about 15% (w/v), about 2% (w/v) to about 12% (w/v), about 2% (w/v) to about 12% (w/v), about 3% (w/v) to about 10% (w/v), about 4% (w/v) to about 10% (w/v), about 4% (w/v) to about 8% (w/v), about 4% (w/v) to about 6% (w/v), about 5% (w/v) to about 10% (w/v), about 6% (w/v) to about 10% (w/v), about 7% (w/v) to about 10% (w/v), about 7% (w/v) to about 9% (w/v), about 8% (w/v) to about 9% (w/v), or about 1.0% (w/v), about 3.0% (w/v), about 5.0% (w/v), or about 8.0% (w/v) relative to the total solution of the liquid formulation, but is not particularly limited thereto. Additionally, the liquid formulation may further include one or more components selected from the group consisting of a non-ionic surfactant and an amino acid, but is not particularly limited thereto.

Accordingly, the stabilizer of the liquid formulation may consist essentially of i) a buffering agent and ii) a saccharide or a sugar alcohol, but may consist essentially of i) a buffering agent, ii) a saccharide or a sugar alcohol, and iii) a non-ionic surfactant; i) a buffering agent, ii) a saccharide or a sugar alcohol, iii) an amino acid; and iv) a non-ionic surfactant; i) a buffering agent, ii) a saccharide or a sugar alcohol, iii) an amino acid; and i) a buffering agent, ii) a saccharide or a sugar alcohol, iii) a non-ionic surfactant, and iv) an amino acid, but is not particularly limited thereto. Here, it is apparent that all of the contents described above or below apply to the type, concentration, or pH of each component constituting the stabilizer.

Although not particularly limited thereto, the non-ionic surfactant, which is one component included in the liquid formulation, lowers the surface tension of the protein solution, thereby preventing protein adsorption or aggregation on the hydrophobic surface.

Specific examples of the non-ionic surfactant that can be used in the present invention may include polysorbates (e.g., polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate); the numerical value 20 after the polyoxyethylene group means the total number of oxyethylene groups —($CH_2CH_2O$)—), poloxamer (PEO-PPO-PEO copolymer; PEO: poly(ethylene oxide), PPO: poly (propylene oxide)), polyethylene-polypropylene glycol, polyoxyethylene compounds (e.g., polyoxyethylene-stearate, polyoxyethylene alkyl ethers (alkyl: $C_1$-$C_{30}$), polyoxyethylene monoallyl ether, alkylphenyl polyoxyethylene copolymer (alkyl: $C_1$-$C_{30}$), etc.), sodium dodecyl sulphate (SDS), etc., or polysorbate or poloxamer. These may also be used alone or a combination of two or more thereof.

Specifically, the non-ionic surfactant may be polysorbate 80, polysorbate 60, polysorbate 40, polysorbate 20, or poloxamer 188, and these may be used in combination, but is not particularly limited thereto.

In the present invention, it is preferable that the non-ionic surfactant is not contained in a high concentration, and specifically, it may be contained in a concentration of about 0.2% (w/v) or less, for example, about 0.001% (w/v) to about 0.2% (w/v), about 0.001% (w/v) to about 0.1% (w/v), about 0.001% (w/v) to about 0.05% (w/v), about 0.005% (w/v) to about 0.08% (w/v), about 0.002% (w/v) to about 0.05% (w/v), about 0.005% (w/v) to about 0.05% (w/v), about 0.01% (w/v) to about 0.05% (w/v), about 0.01% (w/v) to about 0.04% (w/v), about 0.01% (w/v) to about 0.03% (w/v), about 0.01% (w/v) to about 0.1% (w/v), or about 0.02% (w/v), but the concentration is not particularly limited thereto.

The amino acid, which is a type of stabilizer as an optional component that may be added to the liquid formulation, may be methionine, arginine, histidine, glycine, cysteine, lysine, or a combination thereof, but is not limited thereto.

The amino acid may inhibit the generation of impurities that may occur due to the oxidation reaction of the protein, but is not particularly limited thereto.

The amino acid may be present in a concentration of about 0.01 mg/mL to about 1 mg/mL, about 0.01 mg/mL to about 0.8 mg/mL, about 0.01 mg/mL to about 0.5 mg/mL, about 0.02 mg/mL to about 0.5 mg/mL, or about 0.02 mg/mL to about 0.4 mg/mL, or about 0.1 mg/mL in the liquid formulation, but is not particularly limited thereto.

In one embodiment, the liquid formulation including a buffering agent, and a saccharide or a sugar alcohol may or may not include an isotonic agent, and may not further include one or more components selected from the group consisting of a non-ionic surfactant and an amino acid, but is not limited thereto.

Meanwhile, the liquid formulation of the present invention may optionally further include other components or materials known in the art within the range that does not impair the effects of the present invention, in addition to a sugar alcohol, a saccharide, or a combination thereof; and a buffering agent, which are essential components of the above-described liquid formulation; and a non-ionic surfactant and an amino acid, which are optional components, but is not limited thereto.

Meanwhile, the liquid formulation may further include a polyhydric alcohol, but is not particularly limited thereto.

For example, the liquid formulation may include i) a buffering agent and ii) a saccharide or a sugar alcohol as well as a polyhydric alcohol, and may further include a polyhydric alcohol in the stabilizer consisting essentially of i) a buffering agent, ii) a saccharide or a sugar alcohol, and iii) a non-ionic surfactant; i) a buffering agent, ii) a saccharide or a sugar alcohol, iii) an amino acid; and iv) a non-ionic surfactant; i) a buffering agent, ii) a saccharide or a sugar alcohol, iii) an amino acid; and i) a buffering agent, ii) a saccharide or a sugar alcohol, iii) a non-ionic surfactant, and iv) an amino acid.

Examples of polyhydric alcohols that may be further included in the liquid formulation of the present invention may include propylene glycol and low-molecular weight polyethylene glycol, glycerol, low-molecular weight polypropylene glycol, etc., and these may be used in one or two or more combinations thereof, but are not limited thereto.

In the present invention, the long-acting conjugate of Chemical Formula 1 is an active ingredient included in the liquid formulation of the present invention, and may be included therein in a pharmaceutically effective amount. For example, the concentration of the long-acting conjugate in the formulation may be about 18 nmol/mL to about 2,810 nmol/mL, about 18 nmol/mL to about 2,807 nmol/mL, about 18 nmol/mL to about 2,623 nmol/mL, about 18 nmol/mL to about 2,436 nmol/mL, about 18 nmol/mL to about 2,248 nmol/mL, about 18 nmol/mL to about 2,061 nmol/mL, about 18 nmol/mL to about 1,874 nmol/mL, about 18 nmol/mL to about 1,686 nmol/mL, about 18 nmol/mL to about 1,499 nmol/mL, about 18 nmol/mL to about 1,312 nmol/mL, about 18 nmol/mL to about 1,124 nmol/mL, about 18 nmol/mL to about 940 nmol/mL, about 18 nmol/mL to about 936 nmol/mL, about 18 nmol/mL to about 843 nmol/mL, about 18 nmol/mL to about 750 nmol/mL, about 18 nmol/mL to about 656 nmol/mL, about 18 nmol/mL to about 570 nmol/mL, about 18 nmol/mL to about 562 nmol/mL, about 18 nmol/mL to about 469 nmol/mL, about 18 nmol/mL to about 375 nmol/mL, about 18 nmol/mL to about 281 nmol/mL, about 18 nmol/mL to about 188 nmol/mL, about 18 nmol/mL to about 94 nmol/mL, about 187 nmol/mL, about 188 nmol/mL, about 187.09 nmol/mL, about 187.1 nmol/mL, about 93 nmol/mL to about 188 nmol/mL, about 93 nmol/mL to about 281 nmol/mL, about 93 nmol/mL to about 375 nmol/mL, about 93 nmol/mL to about 469 nmol/mL, about 93 nmol/mL to about 562 nmol/mL, about 93 nmol/mL to about 656 nmol/mL, about 93 nmol/mL to about 750 nmol/mL, about 93 nmol/mL to about 843 nmol/mL, about 93 nmol/mL to about 940 nmol/mL, about 93 nmol/mL to about 936 nmol/mL, about 187 nmol/mL to about 281 nmol/mL, about 187 nmol/mL to about 375 nmol/mL, about 187 nmol/mL to about 469 nmol/mL, about 187 nmol/mL to about 570 nmol/mL, or about 187 nmol/mL to about 562 nmol/mL, but is not particularly limited thereto.

As used herein, the term "about" refers to a range which includes all of ±0.5, ±0.4, ±0.3, ±0.2, ±0.1, etc. and includes all of the values that are equivalent or similar to those following the values, but the range is not limited thereto.

In one embodiment, the liquid formulation may be a liquid formulation containing: a peptide conjugate of Chemical Formula 1; a buffering agent selected from citric acid and a salt thereof, acetic acid and a salt thereof, histidine and a salt thereof, phosphoric acid and a salt thereof, and a combination thereof so that the pH of the liquid formulation is 4.8 to 6.5; a saccharide; a non-ionic surfactant selected from poloxamer, polysorbate, or a combination thereof; and a stabilizer selected from the group consisting of methionine, arginine, histidine, glycine, cysteine, lysine, and a combination thereof.

In one embodiment, the liquid formulation may be a liquid formulation containing: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 1% (w/v) to 20% (w/v) of a sugar alcohol, a saccharide, or a combination thereof; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

In one embodiment, the liquid formulation may be a liquid formulation containing: 90 nmol/mL to 562 nmol/mL of a peptide conjugate of Chemical Formula 1; 5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5; 4% (w/v) to 10% (w/v) of a saccharide; 0.01% (w/v) to 0.1% (w/v) of a non-ionic surfactant selected from poloxamer, polysorbate, or a combination thereof; and 0.01 mg/mL to 1 mg/mL of a stabilizer selected from the group consisting of methionine, arginine, histidine, glycine, cysteine, lysine, and a combination thereof.

Meanwhile, hereinafter, the long-acting conjugate of a glucagon derivative peptide, which is an active ingredient included in the liquid formulation of the present invention, will be described in more detail.

As used herein, the term "long-acting conjugate of a glucagon derivative" or "long-acting conjugate of a glucagon derivative peptide" refers to a form in which an immunoglobulin Fc fragment and a glucagon derivative are linked to each other. Specifically, the glucagon derivative may be covalently linked to the immunoglobin Fc fragment by a linker in the conjugate, but is not particularly limited thereto.

The conjugate may exhibit an increased duration of efficacy compared to a peptide, to which an immunoglobulin is not conjugated, and in the present invention, the conjugate according to Chemical Formula 1 of the peptide of General Formula 1 is referred to as a "long-acting conjugate", and may be used interchangeably with a "peptide conjugate" or "long-acting conjugate of Chemical Formula 1".

In one embodiment, the immunoglobulin Fc fragment and X may not be glycosylated, but is not limited thereto.

Meanwhile, the conjugate may be one which does not occur naturally.

The long-acting conjugate of the present invention may be in a form in which the glucagon derivative peptide and the immunoglobulin Fc fragment are linked to each other, and the linking method is not particularly limited thereto, but the peptide and the immunoglobulin Fc fragment may be linked to each other through a linker.

In one embodiment, the long-acting conjugate of the present invention has the structure of Chemical Formula 1 below:

$X\text{-}L_a\text{-}F$ [Chemical Formula 1]

In Chemical Formula 1 above,

X is a peptide of General Formula 1;

L is a linker containing an ethylene glycol repeating unit;

a is 0 or a natural number, with the proviso that when a is 2 or more, each L is independent of each other;

F is an immunoglobulin Fc fragment; and

— represents a covalent bond.

The X of the long-acting conjugate of Chemical Formula 1 may be a peptide having activity for a glucagon derivative. The "peptide having activity for a glucagon derivative" includes various substances having a significant level of activity for a glucagon derivative, for example, various peptides.

More specifically, the peptide having activity for a glucagon derivative is a peptide having activity for a glucagon derivative, including the sequence of General Formula 1 below:

[General Formula 1]

Y—X2-QGTF—X7-SD-X10-S—X12-X13-X14-X15-X16-X17-X18-X19-X20-X21-F—X23-X24-W-L-X27-X28-T-X30 (General Formula 1, SEQ ID NO: 46)

In General Formula 1 above,

X2 is α-methyl-glutamic acid, aminoisobutyric acid (Aib), D-alanine, glycine, Sar (N-methylglycine), serine, or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C), or is absent;

X17 is aspartic acid (D), glutamine (Q), glutamic acid (E), lysine (K), arginine (R), serine (S), cysteine (C), or valine (V), or is absent;

X18 is alanine (A), aspartic acid (D), glutamine (Q), glutamic acid (E), arginine (R), valine (V), or cysteine (C), or is absent;

X19 is alanine (A), arginine (R), serine (S), valine (V), or cysteine (C), or is absent;

X20 is lysine (K), histidine (H), glutamic acid (E), glutamine (Q), aspartic acid (D), arginine (R), α-methyl-glutamic acid, or cysteine (C), or is absent;

X21 is aspartic acid (D), glutamic acid (E), leucine (L), valine (V), or cysteine (C), or is absent;

X23 is isoleucine (I), valine (V), or arginine (R), or is absent;

X24 is valine (V), arginine (R), alanine (A), cysteine (C), glutamic acid (E), lysine (K), glutamine (Q), α-methyl-glutamic acid, or leucine (L), or is absent;

X27 is isoleucine (I), valine (V), alanine (A), lysine (K), methionine (M), glutamine (Q), or arginine (R), or is absent;

X28 is glutamine (Q), lysine (K), asparagine (N), or arginine (R), or is absent;

X30 is cysteine (C), or is absent (with the proviso that when the amino acid sequence of General Formula 1 is identical to SEQ ID NO: 1 and SEQ ID NO: 12, it is excluded).

As the liquid formulation according to any one of the above-described embodiments, in the long-acting conjugate of the glucagon derivative peptide, the glucagon derivative peptide includes the amino acid sequence of General Formula 2 below:

Y-Aib-QGTF—X7-SD-X10-S—X12-Y-L-X15-X16-X17-R-A-X20-X21-F—V—X24-W-L-M-N-T-X30 (General Formula 2, SEQ ID NO: 47)

In General Formula 2 above,

X7 is threonine (T), valine (V), or cysteine (C);

X10 is tyrosine (Y) or cysteine (C);

X12 is lysine (K) or cysteine (C);

X15 is aspartic acid (D) or cysteine (C);

X16 is glutamic acid (E) or serine (S);

X17 is lysine (K) or arginine (R);

X20 is glutamine (Q) or lysine (K);

X21 is aspartic acid (D) or glutamic acid (E);

X24 is valine (V) or glutamine (Q);

X30 is cysteine (C) or is absent (with the proviso that when the amino acid sequence of General Formula 2 is identical to SEQ ID NO: 1 and SEQ ID NO: 12, it is excluded).

The peptide may include an amino acid sequence of SEQ ID NOS: 2 to 11 and 13 to 45 and may consist (essentially) of an amino acid sequence selected from the group consisting of SEQ ID NOS: 2 to 11 and 13 to 45, but is not limited thereto.

Examples of the peptide may include a peptide including or consisting (essentially) of an amino acid sequence selected from the group consisting of SEQ ID NOS: 13, 15, and 36 to 44, but is not particularly limited thereto. In another example, the peptide may be a peptide including or consisting (essentially) of the amino acid sequence selected from the group consisting of SEQ ID NO: 37, but is not particularly limited thereto.

Additionally, the glucagon derivative may include an intramolecular bridge, e.g., a covalent bridge or a non-covalent bridge, and specifically in a form including a ring. It may be in a form where a ring is formed between the glutamic acid at position 16 and the lysine residue at position 20, which are underlined in General Formula 1 above, but is not particularly limited thereto. Non-limiting examples of the ring may include a lactam bridge (or lactam ring).

Further, the peptide according to the present invention may include all of those in the form of the peptide itself, a salt thereof (e.g., a pharmaceutically acceptable salt of the peptide), or a solvate thereof. Additionally, the peptide may be in any pharmaceutically acceptable form.

The kind of the salt is not particularly limited. However, the salt is preferably one that is safe and effective to a subject (e.g., a mammal), but is not particularly limited thereto.

The term "pharmaceutically acceptable" refers to a material which can be effectively used for the intended use within the scope of pharmaco-medical decision without inducing excessive toxicity, irritation, or allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

Additionally, as used herein, the term "solvate" refers to a complex formed between the peptide according to the present invention or a salt thereof and a solvent molecule.

Additionally, although described as "a peptide consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the peptide has an activity the same as or corresponding to that of the peptide which consists of an amino acid sequence of the corresponding SEQ ID NO, and even when the sequence addition or mutation is present, it obviously belongs to the scope of the present invention.

Meanwhile, the peptide may be one which does not occur naturally.

The C-terminus of the peptide may be an amidated peptide or a peptide having a free carboxyl group (—COOH), or may include a peptide having an unmodified C-terminus, but is not limited thereto.

In one embodiment, the X may be amidated at the C-terminus, but is not limited thereto.

In one embodiment, the Q/X may be non-glycosylated, but is not limited thereto.

The peptide of General Formula 1 of the present invention can be synthesized through a solid phase synthesis method, can be produced by a recombinant method, and can be produced by commercially, but is not limited thereto.

As used herein, the term "long-acting conjugate of Chemical Formula 1", being an active ingredient included in the liquid formulation of the present invention, may be included in the liquid formulation in a pharmacologically effective amount. Specifically, the conjugate is in a form, in which the peptide having activity for the glucagon derivative and an immunoglobulin Fc region are linked to each other by a linker, and may exhibit an enhanced duration of efficacy compared to a peptide having activity for the glucagon derivative to which an immunoglobulin Fc region is not linked.

Additionally, in the long-acting conjugate of Chemical Formula 1, the linkage between X, the peptide having activity for the glucagon derivative, and the immunoglobulin Fc fragment may be achieved by a physical or chemical bond, a non-covalent or covalent bond, and specifically, a covalent bond, but is not limited thereto.

Additionally, in the peptide conjugate of Chemical Formula 1, the method of linking X, the peptide having activity for the glucagon derivative, and the immunoglobulin Fc fragment is not particularly limited, but the peptide having activity for the glucagon derivative and the immunoglobulin Fc fragment may be linked to each other through a linker.

Specifically, the long-acting conjugate included in the liquid formulation of the present invention may be one represented by Chemical Formula 1 above.

In Chemical Formula 1 above, X and F may be linked to each other through L by a covalent bond.

More specifically, X and L, and L and F may be linked to each other by a covalent bond, and in particular, the conjugate may be a conjugate in which X, L, and F are each linked by a covalent bond in the order of Chemical Formula 1.

Additionally, X may be directly linked to F (i.e., a is 0 in Chemical Formula 1 above) or may be linked through a linker (L).

In one embodiment, $L_a$, which is one component of the long-acting conjugate of Chemical Formula 1, may be a linker containing an ethylene glycol repeating unit, e.g., (polyethylene glycol), and additionally, those derivatives which are already known in the art and the derivatives that can easily be prepared at the technological level of those skilled in the art are included in the scope of the present invention.

The L, which is a linker containing an ethylene glycol repeating unit, may include a functional group at an end, which is used in the preparation of the conjugate, before it is formed into a conjugate. The long-acting conjugate according to the present invention may be in the form in which X and F are linked through the functional group, but is not limited thereto. In the present invention, the linker containing an ethylene glycol repeating unit may include two, or three or more functional groups, and each functional group may be the same as or different from each other, but is not limited thereto.

Specifically, the linker may be polyethylene glycol (PEG) represented by Chemical Formula 3 below, but is not limited thereto:

[Chemical Formula 3]

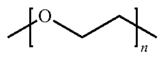

wherein n is 10 to 2,400, n is 10 to 480, or n is 50 to 250, but the range of n is not limited thereto.

In the long-acting conjugate above, the PEG moiety may include not only the $-(CH_2CH_2O)_n-$ structure, but also an oxygen atom interposed between a linking element and the $-(CH_2CH_2O)_n-$ structure, but the PEG moiety is not limited thereto.

The polyethylene glycol is a general term including all of the forms of homopolymers of ethylene glycol, PEG copolymers, and monomethyl-substituted PEG polymers (mPEG), but is not particularly limited thereto.

In one embodiment, the ethylene glycol repeating unit may be represented by, for example, $[OCH_2CH_2]_n$, and the value of n is a natural number and the average molecular weight of the $[OCH_2CH_2]_n$ region in the peptide conjugate, for example, the number average molecular weight, may be determined to be greater than 0 kDa to about 100 kDa, but is not limited thereto. In another example, the value of n is a natural number, and the average molecular weight of the $[OCH_2CH_2]_n$ region in the peptide conjugate, for example, the number average molecular weight, may be about 1 kDa to about 100 kDa, about 1 kDa to about 80 kDa, about 1 kDa to about 50 kDa, about 1 kDa to about 30 kDa, about 1 kDa to about 25 kDa, about 1 kDa to about 20 kDa, about 1 kDa to about 15 kDa, about 1 kDa to about 13 kDa, about 1 kDa to about 11 kDa, about 1 kDa to about 10 kDa, about 1 kDa to about 8 kDa, about 1 kDa to about 5 kDa, about 1 kDa to about 3.4 kDa, about 3 kDa to about 30 kDa, about 3 kDa to about 27 kDa, about 3 kDa to about 25 kDa, about 3 kDa to about 22 kDa, about 3 kDa to about 20 kDa, about 3 kDa to about 18 kDa, about 3 kDa to about 16 kDa, about 3 kDa to about 15 kDa, about 3 kDa to about 13 kDa, about 3 kDa to about 11 kDa, about 3 kDa to about 10 kDa, about 3 kDa to about 8 kDa, about 3 kDa to about 5 kDa, about 3 kDa to about 3.4 kDa, about 8 kDa to about 30 kDa, about 8 kDa to about 27 kDa, about 8 kDa to about 25 kDa, about 8 kDa to about 22 kDa, about 8 kDa to about 20 kDa, about 8 kDa to about 18 kDa, about 8 kDa to about 16 kDa, about 8 kDa to about 15 kDa, about 8 kDa to about 13 kDa, about 8 kDa to about 11 kDa, about 8 kDa to about 10 kDa, about 9 kDa to about 15 kDa, about 9 kDa to about 14 kDa, about 9 kDa to about 13 kDa, about 9 kDa to about 12 kDa, about 9 kDa to about 11 kDa, about 9.5 kDa to about 10.5 kDa, or about 10 kDa, but is not limited thereto.

In one embodiment, both ends of the linker may be bound to a thiol group, an amino group, or a hydroxyl group of the immunoglobulin Fc region, and may be bound to a thiol group, an amino group, an azide group, or a hydroxyl group of the peptide of General Formula 1.

Specifically, the linker may include a reactive group capable of binding to each of the immunoglobulin Fc and the peptide of General Formula 1 at both ends. Specifically, the linker may include a reactive group that can bind to a thiol group of cysteine; an amino group located at the N-terminus, lysine, arginine, glutamine, and/or histidine; and/or a hydroxyl group located at the C-terminus of the immunoglobulin Fc fragment, and that can bind to a thiol group; an amino group of lysine, arginine, glutamine, and/or histidine; an azide group of azido-lysine; and/or a hydroxyl group of the peptide of General Formula 1, but the reactive groups are not limited thereto.

More specifically, the reactive group of the linker may be one or more selected from the group consisting of an aldehyde group, a maleimide group, and a succinimide derivative, but is not limited thereto.

In the above, as an example of the aldehyde group, a propionaldehyde group or butyraldehyde group may be used, but the aldehyde group is not limited thereto.

In the above, as a succinimide derivative, succinimidyl carboxymethyl, succinimidyl valerate, succinimidyl methylbutanoate, succinimidyl methylpropionate, succinimidyl butanoate, succinimidyl propionate, N-hydroxysuccinimide, hydroxy succinimidyl, or succinimidyl carbonate may be used, but the succinimide derivative is not limited thereto.

The linker may be linked to F, the immunoglobulin Fc, and X, the peptide of General Formula 1, through the reactive groups to be converted to a linker moiety.

Additionally, the final product produced through reductive amination by an aldehyde bond is much more stable than that linked by an amide bond. The aldehyde reactive group selectively reacts at the N-terminus at a low pH, while it can form a covalent bond with a lysine residue at a high pH (e.g., pH 9.0), but is not limited thereto.

The terminal reactive groups of the linker of the present invention may be the same as or different from each other. The linker may have an aldehyde reactive group at both ends. Alternatively, the linker may have an aldehyde group and a maleimide group at each end, or may have an aldehyde group and a succinimide reactive group at each end, but is not limited thereto.

For example, the linker may have a maleimide group at one end and an aldehyde group, a propionaldehyde group, or a butyraldehyde group at the other end. As another example, the linker may have a succinimidyl group at one end and a propionaldehyde group or butyraldehyde group at the other end.

When a polyethylene glycol having a hydroxy reactive group at propionaldehyde end is used as a linker, the conjugate of the present invention may be prepared by activating the hydroxy group to various reactive groups by known chemical reactions or by using a commercially available polyethylene glycol having a modified reactive group.

In a specific embodiment, the reactive group of the linker may be linked to a cysteine residue of the peptide of General Formula 1, more specifically to the —SH group of cysteine, but the linker is not limited thereto.

When maleimide-PEG-aldehyde is used, the maleimide group may be linked to the —SH group of the peptide of General Formula 1 by a thioether bond, and the aldehyde group may be linked to the $-NH_2$ group of the immunoglobulin Fc through reductive alkylation, but is not limited thereto, and this is merely an embodiment.

Through the reductive alkylation, a structure such as -PEG-O—$CH_2CH_2CH_2NH$—immunoglobulin Fc may be formed by linking an amino group at the N-terminus of an immunoglobulin Fc fragment to an oxygen atom located at one end of the PEG through a linker reactive group having a structure of $-CH_2CH_2CH_2-$; and a structure, in which one end of the PEG is linked to a sulfur atom located at the cysteine of the peptide of General Formula 1 through a thioether bond, may be formed. The thioether bond described above may include the following structure:

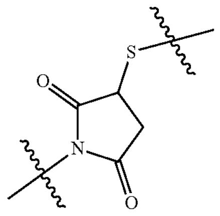

However, the linker is not particularly limited to the above embodiment, and it is merely an embodiment.

Additionally, in the above conjugate, the reactive group of the linker may be linked to —$NH_2$ located at the N-terminus of an immunoglobulin Fc fragment, but this is merely an embodiment.

In addition, in the conjugate, the peptide of General Formula 1 may be linked to a linker having a reactive group through the C-terminus, but this is merely an embodiment.

As used herein, the term "C-terminus" refers to a carboxy terminus of a peptide, and refers to a position capable of binding with the linker for the purpose of the present invention. For example, the C-terminus may include the amino acid residue at the most terminal end of the C-terminus as well as amino acid residues near the C-terminus, and specifically, may include the $1^{st}$ to $20^{th}$ amino acid residues from the most terminal end, although the C-terminus is not limited thereto.

In one embodiment, the conjugate of Chemical Formula 1 may have a structure of Chemical Formula 2 below:

[Chemical Formula 2]

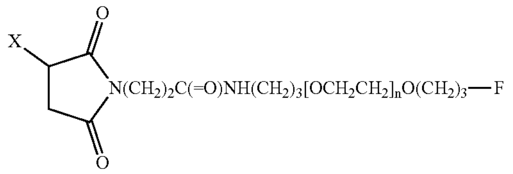

In Chemical Formula 2, X is the peptide of Chemical Formula 1 described above;

F is an immunoglobulin Fc fragment; and n may be a natural number. In particular, the description of n is the same as described above.

In one embodiment, the long-acting conjugate of Chemical Formula 2 has a structure in which the peptide X of General Formula 1 of SEQ ID NO: 46 and the immunoglobulin Fc fragment F are covalently linked through an ethylene glycol repeating unit, wherein each X may be linked to a succinimide ring of Chemical Formula 2, and F may be linked to an oxypropylene group of Chemical Formula 2.

In Chemical Formula 2 above, the value of n may be determined such that the average molecular weight of the $[OCH_2CH_2]_n$ region in the peptide conjugate, for example, the number average molecular weight, is 1 kDa to 100 kDa, or 1 kDa to 20 kDa, or 10 kDa, but not limited thereto.

The X of the peptide conjugate may be a peptide having activity for a glucagon derivative.

In one embodiment, the moiety at which X is linked to the succinimide ring of Chemical Formula 2 may be a sulfur atom of the C-terminal cysteine of X.

The F is a human immunoglobulin Fc fragment, and the human immunoglobulin Fc fragment in the present specification encompasses not only a native sequence obtained from papain digestion of an immunoglobulin, but also derivatives, substituents thereof, for example, variants, in which one or more amino acid residues in the native sequence are modified by deletion, insertion, non-conservative or conservative substitution, or a combination thereof, and thus the sequence become different from the native sequence, etc., provided that the above derivatives, substituents, and variants retain FcRn binding ability.

The moiety linked to the oxypropylene group in F is not specifically limited. In one embodiment of the present invention, the moiety of F linked to the oxypropylene group may be an N-terminal nitrogen or a nitrogen atom of a residue in F (e.g., epsilon nitrogen of lysine). In one specific embodiment of the present invention, the moiety where F is linked to the oxypropylene group of Chemical Formula 1 may be the N-terminal proline of F, but is not limited thereto.

The F may have a structure in which two polypeptide chains are linked by an inter-disulfide bond, and the F is linked through a nitrogen atom in only one of the two chains, but is not limited thereto. The linkage through the nitrogen atom may be linkage to the epsilon amino atom of lysine or the N-terminal amino group by reductive amination, but is not limited thereto.

The reductive amination reaction refers to a reaction in which an amine group or amino group of a reactant reacts with an aldehyde (i.e., a functional group capable of reductive amination) of another reactant to produce an amine, and thereafter, an amine bond is formed by a reduction reaction. The reductive amination reaction is a reaction of organic synthesis widely known in the art.

In one embodiment, the F may be linked through the nitrogen atom of the N-terminal proline thereof, but is not limited thereto.

As a kind of the glucagon derivative peptide, the kind described in International Patent Publication Nos. WO 2016/108586 and WO 2017/003191 may be mentioned, and the entire specification of the International Patent Publications is incorporated herein by reference. Further, the method for preparing the long-acting conjugate of the glucagon derivative peptide is described in WO 2017/003191, and it is obvious that the entire specification of the International Patent Publication is also incorporated herein by reference.

Such a glucagon derivative may be one having improved physical properties by having an altered pI relative to native glucagon. Additionally, the glucagon derivative may be one with improved solubility while having the activity of activating glucagon receptors, but is not limited thereto.

Additionally, the glucagon derivative may be one which does not occur naturally.

Meanwhile, the native glucagon may have the following amino acid sequence:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1)

As used herein, the term "isoelectric point" or "pI" refers to the pH value at which a molecule such as a polypeptide or peptide has no net charge (0). In the case of a polypeptide with various charged functional groups, the net charge of the total polypeptide is "0" at a point where the pH value is the same as that of the pI. The net charge of the polypeptide at a pH higher than the pI will be negative while the net charge of the polypeptide at a pH lower than the pI will be positive.

The pI values may be determined on an immobilized pH gradient gel consisting of polyacrylamide, starch, or agarose by isoelectric electrophoresis, or may be estimated, for example, from an amino acid sequence using a pI/MW tool (http://expasy.org/tools/pi_tool.html; Gasteiger et al., 2003) in an ExPASy server.

As used herein, the term "altered pI" refers to a pI which is different from that of native glucagon due to the substitution of a part of the amino acid sequence of native glucagon with an amino acid residue having a negative charge or a positive charge, i.e., a reduced or increased pI value. The peptide with such an altered pI can exhibit improved solubility and/or high stability at a neutral pH as a glucagon derivative, but is not particularly limited thereto.

More specifically, the glucagon derivative may have an altered pI value, not the pI value (6.8) of native glucagon, and even more specifically, a pI value of less than 6.8, more specifically, 6.7 or less, more specifically 6.5 or less, and additionally, a pI value exceeding 6.8, 7 or higher, more specifically, 7.5 or higher, but is not limited thereto, and any pI value different from that of native glucagon will belong to the scope of the present invention. In particular, when the pI value is different from that of native glucagon and thus exhibits an improved solubility at a neutral pH compared to that of native glucagon, thereby showing a low level of aggregation, it will particularly belong to the scope of the present invention.

More specifically, the glucagon derivative may have a pI value of 4 to 6.5 and/or 7 to 9.5, specifically 7.5 to 9.5, and more specifically, 8.0 to 9.3, but the pI value is not limited thereto. In this case, due to the lower or higher pI value compared to that of native glucagon, an improved solubility and high stability at a neutral pH compared to that of native glucagon can be exhibited, but is not particularly limited thereto.

Specifically, a derivative of native glucagon may be modified by any one method of substitution, addition, deletion, and modification, or a combination thereof in part of the amino acid of native glucagon. Such amino acid substitution may generally occur based on similarity of polarity, charge, solubility, hydrophobicity, hydrophilicity, and/or amphipathic nature of a residue, and conservative substitutions with these amino acids having similar properties can be expected to produce the same or similar activity.

Examples of the glucagon derivatives prepared by a combination of the above methods include a peptide which differs in at least one amino acid residue of the amino acid sequence compared to that of native glucagon and in which the N-terminal amino acid residue is deaminated, having the function of activating a glucagon receptor, etc., but is not limited thereto, and the native glucagon derivatives that are applicable to the present invention can be prepared by a combination of various methods for preparing the derivatives.

Additionally, such modification for the preparation of native glucagon derivatives may include all of the modifications using L-type or D-type amino acids, and/or non-native type amino acids; and/or a modification of native sequence, for example, modification of a functional group, an intramolecular covalent bonding (e.g., a ring formation between side chains), methylation, acylation, ubiquitination, phosphorylation, aminohexanation, biotinylation, etc. Additionally, the modification may also include substitutions into non-native compounds.

Additionally, the native glucagon derivatives may also include modifications of all those where one or more amino acids are added to the amino and/or carboxy terminal of native glucagon.

As for the amino acids being substituted or added, not only the 20 amino acids commonly found in human proteins, but also atypical amino acids or those which do not occur naturally can be used. Commercial sources of atypical amino acids may include Sigma-Aldrich, ChemPep Inc., and Genzyme Pharmaceuticals. The peptides including these amino acids and typical peptide sequences may be synthesized and purchased from commercial suppliers, e.g., American Peptide Company, Bachem (USA), or Anygen (Korea).

Amino acid derivatives may also be obtained in a similar manner, for example, 4-imidazoacetic acid, etc., may be used.

Since glucagon has a pH of about 7, it is insoluble in a solution having a physiological pH (pH 4 to 8) and tends to precipitate at a neutral pH. In an aqueous solution with a pH of 3 or below, glucagon is dissolved at the initial stage but precipitates within one hour by forming a gel. Since the gelated glucagon mainly consists of β-sheet fibrils, the administration of the thus-precipitated glucagon via an injection needle or intravenous injection will block blood vessels, and thus is not suitable for use as an injection agent. In order to delay the precipitation process, acidic (pH 2 to 4) formulations are commonly used, and by doing so, glucagon can be maintained in a relatively non-aggregated state for a short period of time. However, glucagon can form fibrils very rapidly at a low pH, and thus these acidic formulations must be injected upon preparation.

In this regard, the present inventors have developed glucagon derivatives with extended action profiles by modifying the pI of native glucagon via substitution of amino acid residues having negative charges and positive charges. The glucagon derivatives of the present invention, by having an altered pI compared to that of native glucagon, are characterized in having improved solubility and/or high stability at a neutral pH, compared to that of native glucagon.

In a specific embodiment of the present invention, the glucagon derivative may be a peptide which includes the amino acid sequence of General Formula 1 below:

Y—X2-QGTF-X7-SD-X10-S—X12-X13-X14-X15-X16-X17-X18-X19-X20-X21-F—X23-X24-W-L-X27-X28-T-X30 (General Formula 1, SEQ ID NO: 46)

In the above General Formula,

X2 is α-methyl-glutamic acid, aminoisobutyric acid (Aib), D-alanine, glycine, Sar (N-methylglycine), serine, or D-serine;

X7 is threonine, valine, or cysteine;

X10 is tyrosine or cysteine;

X12 is lysine or cysteine;

X13 is tyrosine or cysteine;

X14 is leucine or cysteine;

X15 is aspartic acid, glutamic acid, or cysteine;

X16 is glutamic acid, aspartic acid, serine, α-methyl-glutamic acid, or cysteine, or is absent;

X17 is aspartic acid, glutamine, glutamic acid, lysine, arginine, serine, cysteine, or valine, or is absent;

X18 is alanine, aspartic acid, glutamic acid, glutamine, arginine, valine, or cysteine, or is absent;

X19 is alanine, arginine, serine, valine, or cysteine, or is absent;

X20 is lysine, histidine, glutamic acid, glutamine, aspartic acid, arginine, α-methyl-glutamic acid, or cysteine, or is absent;

X21 is aspartic acid, glutamic acid, leucine, valine, or cysteine, or is absent;

X23 is isoleucine, valine, or arginine, or is absent;

X24 is valine, arginine, alanine, cysteine, glutamic acid, lysine, glutamine, α-methyl-glutamic acid, or leucine, or is absent;

X27 is isoleucine, valine, alanine, lysine, methionine, glutamine, or arginine, or is absent;
X28 is glutamine, lysine, asparagine, or arginine, or is absent; and
X30 is cysteine or is absent (with the proviso that when the amino acid sequence of General Formula 1 is identical to SEQ ID NO: 1 and SEQ ID NO: 12, it is excluded).

More specifically,
in General Formula 1 above,
X2 is serine or aminoisobutyric acid (Aib);
X7 is threonine, valine, or cysteine;
X10 is tyrosine or cysteine;
X12 is lysine or cysteine;
X13 is tyrosine or cysteine;
X14 is leucine or cysteine;
X15 is aspartic acid or cysteine;
X16 is glutamic acid, serine, or cysteine;
X17 is aspartic acid, glutamic acid, lysine, arginine, serine, cysteine, or valine;
X18 is aspartic acid, glutamic acid, arginine, or cysteine;
X19 is alanine or cysteine;
X20 is glutamine, aspartic acid, lysine, or cysteine;
X21 is aspartic acid, glutamic acid, leucine, valine, or cysteine;
X23 is isoleucine, valine, or arginine;
X24 is valine, arginine, alanine, glutamic acid, lysine, glutamine, or leucine;
X27 is isoleucine, valine, alanine, methionine, glutamine, or arginine;
X28 is glutamine, lysine, asparagine, or arginine; and
X30 is cysteine or is absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 2 to 45, and specifically, one which consists (essentially) of an amino acid sequence selected from the group consisting of SEQ ID NOS: 2 to 45, but is not limited thereto.

Additionally, although described as "a peptide consisting of a particular SEQ ID NO" in the present invention, it does not exclude a mutation that may occur by the addition of a meaningless sequence upstream or downstream of the amino acid sequence of the corresponding SEQ ID NO, or a mutation that may occur naturally, or a silent mutation thereof, as long as the peptide has an activity the same as or corresponding to that of the peptide which consists of an amino acid sequence of the corresponding SEQ ID NO, and even when the sequence addition or mutation is present, it obviously belongs to the scope of the present invention.

Those described above may be also applied to other specific embodiments or aspects of the present invention, but are not limited thereto.

Specifically, in General Formula 1 above,
X2 may be serine or aminoisobutyric acid (Aib);
X7 may be cysteine, threonine, or valine;
X10 may be tyrosine or cysteine;
X12 may be lysine or cysteine;
X13 may be tyrosine or cysteine;
X14 may be leucine or cysteine;
X15 may be aspartic acid or cysteine;
X16 may be glutamic acid, serine, or cysteine;
X17 may be glutamic acid, lysine, arginine, cysteine, or valine;
X18 may be arginine or cysteine;
X19 may be alanine or cysteine;
X20 may be glutamine or lysine;
X21 may be aspartic acid, glutamic acid, valine, or cysteine;
X23 may be valine;
X24 may be valine or glutamine;
X27 may be methionine;
X28 may be asparagine or arginine; and
X30 may be cysteine or is absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 3, 11 to 17, 19 to 27, 29, 31, 33, and 35 to 44, and specifically, one which consists (essentially) of an amino acid sequence selected from the group consisting of SEQ ID NOS: 3, 11 to 17, 19 to 27, 29, 31, 33, and 35 to 44, but is not limited thereto.

Specifically, in General Formula 1 above,
X2 may be aminoisobutyric acid (Aib);
X7 may be cysteine, threonine, or valine;
X10 may be tyrosine or cysteine;
X12 may be lysine;
X13 may be tyrosine or cysteine;
X14 may be leucine or cysteine;
X15 may be aspartic acid or cysteine;
X16 may be glutamic acid, serine, or cysteine;
X17 may be lysine, arginine, cysteine, or valine;
X18 may be arginine or cysteine;
X19 may be alanine or cysteine;
X20 may be glutamine or lysine;
X21 may be aspartic acid, glutamic acid, or cysteine;
X23 may be valine;
X24 may be glutamine;
X27 may be methionine;
X28 may be asparagine or arginine; and
X30 may be cysteine or is absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 14, 17, 19 to 25, 27, 29, 33, 35 to 38, 40 to 42, and 44, and specifically, one which consists (essentially) of an amino acid sequence selected from the group consisting of SEQ ID NOS: 14, 17, 19 to 25, 27, 29, 33, 35 to 38, 40 to 42, and 44, but is not limited thereto.

Specifically, in General Formula 1 above,
X2 may be serine or aminoisobutyric acid (Aib);
X7 may be threonine, valine, or cysteine;
X10 may be tyrosine or cysteine;
X12 may be lysine or cysteine;
X13 may be tyrosine or cysteine;
X14 may be leucine or cysteine;
X15 may be aspartic acid or cysteine;
X16 may be glutamic acid, serine, or cysteine;
X17 may be aspartic acid, glutamic acid, lysine, arginine, serine, cysteine, or valine;
X18 may be aspartic acid, glutamic acid, arginine, or cysteine;
X19 may be alanine or cysteine;
X20 may be glutamine, aspartic acid, or lysine;
X21 may be aspartic acid or glutamic acid;
X23 may be valine;
X24 may be valine or glutamine;

X27 may be isoleucine or methionine;
X28 may be asparagine or arginine;
X29 may be threonine; and
X30 may be cysteine or may be absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 2 to 13, 15, 17, 20 to 24, 26 to 30, and 32 to 44, and specifically, one which consists (essentially) of an amino acid sequence selected from the group consisting of SEQ ID NOS: 2 to 13, 15, 17, 20 to 24, 26 to 30, and 32 to 44, but is not limited thereto.

Specifically, in the General Formula 1 above,
X2 may be aminoisobutyric acid (Aib);
X7 may be threonine;
X10 may be tyrosine;
X12 may be lysine;
X13 may be tyrosine;
X14 may be leucine;
X15 may be aspartic acid or cysteine;
X16 may be glutamic acid, serine, or cysteine;
X17 may be lysine or arginine;
X18 may be arginine;
X19 may be alanine;
X20 may be glutamine, cysteine, or lysine;
X21 may be aspartic acid, cysteine, valine, or glutamic acid;
X23 may be valine or arginine;
X24 may be glutamine or leucine;
X27 may be methionine;
X28 may be asparagine or arginine;
X29 may be threonine; and
X30 may be absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 14, 16, 18, 19, 25, and 31, and specifically, one which consists (essentially) of an amino acid sequence selected from the group consisting of SEQ ID NOS: 14, 16, 18, 19, 25, and 31, but is not limited thereto.

More specifically, the glucagon derivative peptide may be a peptide which includes the amino acid sequence of General Formula 2 below:

Y-Aib-QGTF-X7-SD-X10-S—X12-Y-L-X15-X16-X17-R-A-X20-X21-F—V—X24-W-L-M-N-T-X30 (General Formula 2, SEQ ID NO: 47)

In General Formula 2 above,
X7 may be threonine, valine, or cysteine;
X10 may be tyrosine or cysteine;
X12 may be lysine or cysteine;
X15 may be aspartic acid or cysteine;
X16 may be glutamic acid or serine;
X17 may be lysine or arginine;
X20 may be glutamine or lysine;
X21 may be aspartic acid or glutamic acid;
X24 may be valine or glutamine; and
X30 may be cysteine or may be absent (with the proviso that when the amino acid sequence of General Formula 1 is identical to SEQ ID NO: 1 and SEQ ID NO: 12, it is excluded).

For example, the glucagon derivative peptide may be one which includes an amino acid sequence selected from the group consisting of SEQ ID NOS: 13, 15, and 36 to 44, and specifically, one which consists (essentially) of an amino acid sequence selected from the group consisting of SEQ ID NOS: 13, 15, and 36 to 44, but is not limited thereto. More specifically, the peptide may be one which includes an amino acid sequence of SEQ ID NO: 20 or SEQ ID NO: 37, or consists (essentially) of the corresponding amino acid sequence, but is not limited thereto.

Specifically, in General Formula 2 above,
X7 may be threonine, valine, or cysteine;
X10 may be tyrosine or cysteine;
X12 may be lysine;
X15 may be aspartic acid;
X16 may be glutamic acid or serine;
X17 may be lysine or arginine;
X20 may be glutamine or lysine;
X21 may be aspartic acid or glutamic acid;
X24 may be glutamine; and
X30 may be cysteine or may be absent (with the proviso that when the amino acid sequence of General Formula 1 is identical to SEQ ID NO: 1 and SEQ ID NO: 12, it is excluded), but is not particularly limited thereto.

For example, the peptide may be one which includes an amino acid sequence selected from the group consisting of SEQ ID NOS: 36 to 38, 40 to 42, and 44, and specifically, one which consists (essentially) of an amino acid sequence selected from the group consisting of SEQ ID NOS: 36 to 38, 40 to 42, and 44, but is not limited thereto.

The glucagon derivative described above may include an intramolecular bridge, (e.g., a covalent bridge or a non-covalent bridge), and specifically in a form including a ring. For example, a ring may be formed between the amino acids at positions 16 and 20 of the glucagon derivative, but is not particularly limited thereto.

Non-limiting examples of the ring may include a lactam bridge (or lactam ring).

In addition, the glucagon derivative includes all those modified to include an amino acid capable of forming a ring at a desired position so as to include a ring.

Such a ring may be formed between the amino acid side chains in the glucagon derivative, for example, a lactam ring may be formed between the lysine side chain and the glutamic acid side chain, but is not particularly limited thereto.

For example, the peptide including the amino acid sequence of General Formula 1 or 2 above may be one in which each amino acid in each acid pair among the amino acid pairs of X10 and X14, X12 and X16, X16 and X20, X17 and X21, X20 and X24, and X24 and X28 of General Formula 1 or 2 may be substituted with glutamic acid or lysine, but is not limited thereto. In the $X_n$ (n is an integer), n refers to the position of the amino acid from the N-terminus of an amino acid sequence provided.

Additionally, the peptide including the amino acid sequence of General Formula 1 or 2 may be one in which each amino acid in each amino acid pair of X12 and X16 or the amino acid pair of X16 and X20 or the amino acid pair of X17 and X21 is respectively substituted with glutamic acid or lysine, which is capable of forming a ring.

Additionally, in General Formula 1 or 2, the peptide may be one in which a ring (e.g., a lactam ring) is formed between each amino acid in each amino acid pair in at least one amino acid pair among the amino acid pairs of X10 and X14, X12 and X16, X16 and X20, X17 and X21, X20 and X24, and X24 and X28, but is not limited thereto.

Additionally, in General Formula 1 or 2, X16 may be glutamic acid, X20 may be lysine, and the side chains of X16 and X20 may form a lactam ring, but they are not limited thereto.

Additionally, the glucagon derivative peptide according to the present invention may be in the form where the N-terminus and/or C-terminus is not modified, however, those variants, where the amino terminus and/or carboxy terminus, etc., of the peptide is chemically modified or protected by organic groups, or where amino acids are added to the end of the peptide for its protection from proteases in vivo while increasing its stability, may also be included in the scope of the peptides of the present invention. In a case where the C-terminus is not modified, the end of the peptide according to the present invention may have a carboxyl group, but is not particularly limited thereto.

In particular, in the case of a chemically-synthesized peptide, its N- and C-termini are electrically charged and thus the N- and C-termini of the peptide may be acetylated and/or amidated, but the peptide is not particularly limited thereto.

Unless specified otherwise in the present invention, the description in the detailed description or claims with respect to "the glucagon derivative peptide" according to the present invention or a "conjugate", in which such a peptide is covalently linked to an immunoglobulin Fc fragment, may be applied to the forms, which include not only include the corresponding peptide or conjugate but also the salts of the corresponding peptide or conjugate (e.g., pharmaceutically acceptable salts thereof), or solvates thereof. Accordingly, even in a case where a "peptide" or "conjugate" is described in the present invention, the description may also be equally applied to a particular salt thereof, a particular solvate thereof, and a particular solvate of the particular salt thereof. These salts may be, for example, in a form where any pharmaceutically acceptable salts are used. The kind of the salt is not particularly limited. However, the salt is preferably one that is safe and effective to a subject, e.g., a mammal, but is not particularly limited thereto.

As used herein, the term "immunoglobulin Fc fragment" refers to a heavy chain constant region excluding the heavy and light chain variable regions of an immunoglobulin. Specifically, the immunoglobulin Fc fragment may include the heavy chain constant region 2 (CH2) and/or heavy chain constant region 3 (CH3) portions, and more specifically, may further include a hinge region (all or part of the hinge region).

The immunoglobulin Fc fragment may be a constitution constituting the moiety of the peptide conjugate of Chemical Formula 1 of the present invention. Specifically, it may correspond to F in the Chemical Formula 1 above. Such an immunoglobulin Fc fragment may include a hinge region in the heavy chain constant region, but is not limited thereto.

In the present invention, the immunoglobulin Fc fragment may include a specific hinge sequence in the N-terminus.

As used herein, the term "hinge sequence" refers to a region which is located in the heavy chain and forms a dimer of immunoglobulin Fc fragments through an inter-disulfide bond.

In the present invention, the hinge sequence may be modified such that a part of the hinge sequence having the following amino acid sequence is deleted and thus there is only one cysteine residue in the sequence, but is not limited thereto:

Glu-Ser-Lys-Tyr-Gly-Pro-Pro-Cys-Pro-Ser-Cys-Pro (SEQ ID NO: 48).

The hinge sequence may be one in which the $8^{th}$ or $11^{th}$ cysteine residue in the hinge sequence of SEQ ID NO: 48 is deleted and thus only one cysteine residue is included in the sequence. The hinge sequence of the present invention may consist of 3 to 12 amino acids, including only one cysteine residue, but the hinge sequence is not limited thereto. More specifically, the hinge sequence of the present invention may have the following sequences: Glu-Ser-Lys-Tyr-Gly-Pro-Pro-Pro-Ser-Cys-Pro (SEQ ID NO: 52), Glu-Ser-Lys-Tyr-Gly-Pro-Pro-Cys-Pro-Ser-Pro (SEQ ID NO: 53), Glu-Ser-Lys-Tyr-Gly-Pro-Pro-Cys-Pro-Ser (SEQ ID NO: 54), Glu-Ser-Lys-Tyr-Gly-Pro-Pro-Cys-Pro-Pro (SEQ ID NO: 55), Lys-Tyr-Gly-Pro-Pro-Cys-Pro-Ser (SEQ ID NO: 56), Glu-Ser-Lys-Tyr-Gly-Pro-Pro-Cys (SEQ ID NO: 57), Glu-Lys-Tyr-Gly-Pro-Pro-Cys (SEQ ID NO: 58), Glu-Ser-Pro-Ser-Cys-Pro (SEQ ID NO: 59), Glu-Pro-Ser-Cys-Pro (SEQ ID NO: 60), Pro-Ser-Cys-Pro (SEQ ID NO: 61), Glu-Ser-Lys-Tyr-Gly-Pro-Pro-Ser-Cys-Pro (SEQ ID NO: 62), Lys-Tyr-Gly-Pro-Pro-Pro-Ser-Cys-Pro (SEQ ID NO: 63), Glu-Ser-Lys-Tyr-Gly-Pro-Ser-Cys-Pro (SEQ ID NO: 64), Glu-Ser-Lys-Tyr-Gly-Pro-Pro-Cys (SEQ ID NO: 65), Lys-Tyr-Gly-Pro-Pro-Cys-Pro (SEQ ID NO: 66), Glu-Ser-Lys-Pro-Ser-Cys-Pro (SEQ ID NO: 67), Glu-Ser-Pro-Ser-Cys-Pro (SEQ ID NO: 68), Glu-Pro-Ser-Cys (SEQ ID NO: 69), SEQ ID NO: 49 (Ser-Cys-Pro), or SEQ ID NO: 50 (Pro-Ser-Cys-Pro). More specifically, the hinge sequence may include the amino acid sequence of SEQ ID NO: 49 (Ser-Cys-Pro) or SEQ ID NO: 50 (Pro-Ser-Cys-Pro), but is not limited thereto.

The immunoglobulin Fc fragment of the present invention may be in a form in which two molecules of the immunoglobulin Fc chain form a dimer due to the presence of a hinge sequence therein, and in addition, the long-acting conjugate of Chemical Formula 1 of the present invention may be in a form in which one end of the linker is linked to one chain of the dimeric immunoglobulin Fc fragments, but the immunoglobulin Fc fragment and the conjugate are not limited thereto.

As used herein, the term "N-terminus" refers to the amino terminus of a protein or polypeptide, and it may include 1, 2, 3, 4, 5, 6, 7, 8, 9, or 10 or more amino acids from the most terminal end or the most terminal end of the amino terminus. The immunoglobulin Fc fragment of the present invention may include a hinge sequence in the N-terminus, but is not limited thereto.

Additionally, the immunoglobulin Fc fragment of the present invention may be an extended Fc fragment, which includes all or part of the heavy chain constant region 1 (CH1) and/or light chain constant region 1 (CL1) excluding the heavy chain and light chain variable regions of an immunoglobulin, as long as it has substantially the equivalent or an improved effect compared to its native type. Additionally, the immunoglobulin Fc fragment of the present invention may be a region in which some fairly long amino acid sequences corresponding to CH2 and/or CH3 are removed.

For example, the immunoglobulin Fc fragment of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination of (i) one or two or more domains among a CH1 domain, a CH2 domain, a CH3 domain, and a CH4 domain and (ii) an immunoglobulin hinge region (or part of the hinge region); or 6) a dimer of each domain of the heavy chain constant region and a light chain constant region, but the immunoglobulin Fc region is not limited thereto.

Additionally, in one embodiment, the immunoglobulin Fc fragment may have a dimeric form, and one molecule of the peptide of General Formula 1 may be covalently linked to one Fc region in a dimeric form, in particular, the immunoglobulin Fc and the peptide of General Formula 1 may be covalently linked to each other through a linker containing an ethylene glycol repeating unit. Meanwhile, it is also possible that two molecules of the peptide of General Formula 1 are symmetrically conjugated to one Fc region in a dimeric form. In particular, the immunoglobulin Fc and the peptide of General Formula 1 may be linked to each other through a linker containing an ethylene glycol repeating unit, but is not limited to the embodiments described above.

In addition, the immunoglobulin Fc fragment of the present invention includes native amino acid sequences as well as sequence derivatives thereof. The amino acid sequence derivative means that the sequence is different from the native amino acid sequence due to deletion, insertion, non-conservative or conservative substitution, or a combination thereof in one or more amino acid residues in the native amino acid sequence.

For example, amino acid residues at positions 214 to 238, 297 to 299, 318 to 322, or 327 to 331 in IgG Fc, which are known to be important for linkage, may be used as the sites suitable for variation Additionally, various types of derivatives are available, for example, one where the site capable of forming an inter-disulfide bond is removed; one where several N-terminal amino acids from native Fc are removed; one where a methionine residue is added to the N-terminus of native Fc, etc. Additionally, complement binding sites (e.g., C1q binding sites) or antibody-dependent cell-mediated cytotoxicity (ADCC) sites may be removed to eliminate the effector function. The techniques for preparing the sequence derivatives of these immunoglobulin Fc fragments are disclosed in International Publication Nos. WO 97/34631, WO 96/32478, etc.

Amino acid substitutions in a protein or peptide that do not alter the entire activity of a molecule are well known in the art (H. Neurath, R. L. Hill, *The Proteins*, Academic Press, New York, 1979). The most common substitutions occur between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, amino acids may be modified by phosphorylation, sulfation, acrylation, glycosylation, methylation, farnesylation, acetylation, amidation, etc.

The Fc derivatives described above may be those which exhibit the same biological activity as the Fc fragment of the present invention and have an increased structural stability of the Fc fragment against heat, pH, etc.

Additionally, such an Fc fragment may be obtained from a native type isolated from humans or animals (e.g., cows, goats, pigs, mice, rabbits, hamsters, rats, guinea pigs, etc.) or may be recombinants or derivatives thereof obtained from transformed animal cells or microorganisms. In particular, the Fc region may be obtained from a native immunoglobulin by isolating a whole immunoglobulin from a living human or animal and treating the isolated immunoglobulin with protease. When the whole immunoglobulin is treated with papain, it is cleaved into Fab and Fc fragments, whereas when treated with pepsin, it is cleaved into pF'c and $F(ab)_2$ fragments. Fc or pF'c can be isolated using size exclusion chromatography, etc. In a more specific embodiment, the Fc fragment may be a recombinant immunoglobulin Fc fragment where a human-derived Fc fragment is obtained from a microorganism.

Additionally, the immunoglobulin Fc fragment may be in the form of native glycans, increased or decreased glycans compared to the native type, or in a deglycosylated form. The increase, decrease, or removal of the immunoglobulin Fc glycans may be achieved by conventional methods such as a chemical method, enzymatic method, and genetic engineering method using a microorganism. In particular, the immunoglobulin Fc fragment where the glycans are removed from the Fc shows a significant decrease in binding affinity for the complement (C1q) and a decrease or removal of antibody-dependent cytotoxicity or complement-dependent cytotoxicity, and thus it does not induce unnecessary immune responses in vivo. In this regard, an immunoglobulin Fc fragment in a deglycosylated or aglycosylated form may be more suitable to meet the original object of the present invention as a drug carrier.

As used herein, the term “deglycosylation” refers to an Fc fragment in which glycans are removed with an enzyme, and the term “aglycosylation” refers to a non-glycosylated Fc fragment produced in prokaryotes, and in a more specific embodiment, *E. coli.*

Meanwhile, the immunoglobulin Fc fragment may be derived from humans or animals (e.g., cows, goats, pigs, mice, rabbits, hamsters, rats, guinea pigs, etc.), and in a more specific embodiment, it may be derived from humans.

Additionally, the immunoglobulin Fc fragment may be derived from IgG, IgA, IgD, IgE, IgM, or a combination or hybrid thereof. In a more specific embodiment, the immunoglobulin Fc fragment may be derived from IgG or IgM, which are among the most abundant proteins in human blood, and in an even more specific embodiment, it may be derived from IgG, which is known to enhance the half-lives of ligand-binding proteins. In an even yet more specific embodiment, the immunoglobulin Fc fragment may be an IgG4 Fc fragment, and in the most specific embodiment, it may be an aglycosylated Fc fragment derived from a human IgG4, but is not limited thereto.

Additionally, in a specific embodiment, the immunoglobulin Fc fragment, being a human IgG4 Fc fragment, may be in the form of a homodimer in which two monomers are linked through an inter-disulfide bond (an inter-chain form) between cysteines, which are the $3^{rd}$ amino acid of each monomer. In particular, each monomer of the homodimer independently has/or can have an intra-disulfide bond between the cysteines at positions 35 and 95; and an intra-disulfide bond between the cysteines at positions 141 and 199 (i.e., two internal disulfide bonds (an intra-chain form)). With respect to the number of amino acids, each monomer may consist of 221 amino acids, and the amino acids forming the homodimer may consist of a total of 442 amino acids, but the number of amino acids is not limited thereto. Specifically, the immunoglobulin Fc fragment may be one in which two monomers having the amino acid sequence of SEQ ID NO: 79 (consisting of 221 amino acids) form a homodimer through an inter-disulfide bond between cysteines, which are the $3^{rd}$ amino acid of each monomer, and in which the monomers of the homodimer independently form an internal disulfide bond between the cysteines at positions 35 and 95 and an internal disulfide bond between the cysteines at positions 141 and 199, but the immunoglobulin Fc fragment is not limited thereto.

The F in Chemical Formula 1 may include a monomer of the amino acid sequence of SEQ ID NO: 51, and the F may be a homodimer of the monomers of the amino acid sequence of SEQ ID NO: 51, but is not limited thereto.

In one example, the immunoglobulin Fc fragment may be a homodimer including the amino acid sequence of SEQ ID NO: 70 (consisting of 442 amino acids), but is not limited thereto.

Meanwhile, as used herein, the term “combination” means that polypeptide encoding single-chain immunoglobulin Fc fragment of the same origin is linked to \ single-chain polypeptides of a different origin to form a dimer or multimer. That is, it is possible to prepare a dimer or multimer from two or more fragments selected from the group consisting of IgG Fc fragment, IgA Fc fragment, IgM Fc fragment, IgD Fc fragment, and IgE Fc fragment.

As used herein, the term “hybrid” means that sequences corresponding two or more immunoglobulin Fc fragments of different origins are present in a single chain of an immunoglobulin constant region. In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

Meanwhile, IgG may also be divided into the IgG1, IgG2, IgG3, and IgG4 subclasses, and the present invention may include combinations or hybrids thereof. Preferred are the IgG2 and IgG4 subclasses, and most preferred is the Fc fragment of IgG4, which rarely has effector functions such as complement-dependent cytotoxicity (CDC).

Meanwhile, the liquid formulation may be for prevention or treatment of congenital hyperinsulinism, hypoglycemia or metabolic syndrome.

As used herein, the term “prevention” refers to all activities that inhibit or delay the occurrence of a desired disease, e.g., congenital hyperinsulinism, hypoglycemia or metabolic syndrome, by administering the above glucagon derivative, a conjugate including the same, or a composition, and the term “treatment” refers to all activities that improve or advantageously change the symptoms of a desired disease, e.g., congenital hyperinsulinism, hypoglycemia or metabolic syndrome by administering the above glucagon derivative, a conjugate including the same, or a composition.

As used herein, the term “administration” refers to the introduction of a particular material into a patient by any appropriate method, and the administration route of the composition is not particularly limited, but may be any conventional route that enables delivery of the composition to the target in the body (e.g., intraperitoneal administration, intravenous administration, intramuscular administration, subcutaneous administration, intradermal administration, oral administration, topical administration, intranasal administration, intrapulmonary administration, intrarectal administration, etc.).

As used herein, the term “hypoglycemia” refers to a health state, in which blood glucose levels are lower than those of normal people, and in general, refers to a state when the blood glucose levels are 50 mg/dL or less, but is not particularly limited thereto. Hypoglycemia is frequently caused when a person who takes an oral hypoglycemic agent or insulin has eaten less than usual or has performed activities or exercised more than usual. Additionally, hypoglycemia may occur due to drinking of alcohols, use of glucose level-lowering drugs, severe physical diseases, hormone deficiency such as adrenocortical hormones and glucagon, tumor in insulin-producing pancreas, insulin autoimmune disease, gastrectomy patients, inborn error of carbohydrate metabolism disorder, etc.

In the present invention, the hypoglycemia includes both acute and chronic hypoglycemia.

Symptoms of hypoglycemia include weakness, trembling, pale skin, cold sweat, dizziness, excitement, anxiety, pounding heart, empty stomach, headache, fatigue, etc. In the case of persistent hypoglycemia, it may lead to convulsion or seizure, and may cause shock and thus fainting.

More specifically, the hypoglycemia may be caused by persistent hyperinsulinism due to a genetic defect. Examples of known causes of hyperinsulinism due to a genetic defect may include a mutation on SUR gene or Kir6.2 gene localized on chromosome 11p15.1, or an increase of glucokinase (GK) activity due to a mutation on GK gene localized on chromosome 7p15-p13, an activation of GDH due to a mutation on glutamate dehydrogenase (GDH) gene, leading to an increase of ATP in islet β-cells, etc.

Meanwhile, congenital hyperinsulinism is one of the leading causes of severe and persistent hypoglycemia in newborns and children. It may be caused by an abnormal function of pancreatic cells due to a temporary increase of insulin secretion or genetic mutation in low-birth-weight infants or infants from diabetic mothers, etc. It is known that glucagon may be used for the treatment of the congenital hyperinsulinism.

Additionally, the glucagon derivative of the present invention or a conjugate including the same may be used as a pharmaceutical medicament not only for preventing body weight increase, promoting body weight decrease, reducing overweight, and treating obesity including morbid obesity (e.g., by controlling appetite, ingestion, food intake, calorie intake, and/or energy consumption), but also for treating obesity-related inflammation, obesity-related gallbladder disease, and obesity-induced sleep apnea, but is not limited thereto, and may be used for treating the associated diseases or health conditions thereof. The glucagon derivative of the present invention or a conjugate including the same may also be used for treating metabolic syndrome other than obesity, i.e., obesity-related diseases such as impaired glucose tolerance, hypercholesterolemia, dyslipidemia, obesity, hypertension, non-alcoholic steatohepatitis (NASH), atherosclerosis caused by dyslipidemia, atherosclerosis, arteriosclerosis, coronary heart disease, stroke, etc. However, the effects of the glucagon derivative or a conjugate thereof according to the present invention may be mediated entirely or partially by the body weight-related effects described above or may be independent of the same.

Another aspect for implementing the present invention provides a method for preparing the liquid formulation.

The liquid formulation and components constituting the same are as described above.

Specifically, the preparation method may include: mixing (i) a long-acting conjugate of a glucagon derivative peptide, in which a glucagon derivative peptide and an immunoglobulin Fc fragment are linked to each other, with (ii) a stabilizer including (a) a buffering agent and (b) sugar alcohol, saccharide or a combination.

The stabilizer may further include one or more components selected from the group consisting of a saccharide or a sugar alcohol, a non-ionic surfactant, and an amino acid, and more specifically, may further include a saccharide or a sugar alcohol, an amino acid, or both. For example, the stabilizer may include a buffering agent, a saccharide or a sugar alcohol, and an amino acid, but is not limited thereto.

The long-acting binder, buffering agent, saccharide, sugar alcohol or a combination thereof, non-ionic surfactant, amino acid, and albumin-free stabilizer are the same as described above.

Still another aspect for implementing the present invention provides the use of the liquid formulation in the preparation of a medicament for the prevention or treatment of congenital hyperinsulinism, hypoglycemia or metabolic syndrome.

Yet another aspect for implementing the present invention provides the use of the liquid formulation for use in the prevention or treatment of congenital hyperinsulinism, hypoglycemia or metabolic syndrome.

Even another aspect for implementing the present invention provides a method for preventing or treating congenital hyperinsulinism, hypoglycemia or metabolic syndrome, including: administering the liquid formulation to a subject in need thereof.

The liquid formulation, congenital hyperinsulinism, hypoglycemia, and metabolic syndrome are as described above.

The subject refers to a subject in need of administration of the liquid formulation of the present invention, and includes, without limitation, any subject that can be treated with the liquid formulation of the present invention, and specifically includes humans or mammals including rats, livestock, etc.

The treatment method of the present invention may include administering the liquid formulation in a pharmaceutically effective amount. An appropriate total daily dose of the liquid formulation may be determined within the scope of correct medical judgment by a practitioner, and the liquid formulation may be administered once or several times in divided doses. However, for the purpose of the present invention, it is preferred that the specific therapeutically effective dose of the liquid formulation for any particular patient be applied differently depending on the kind and degree of responses to be achieved, specific compositions including whether other agents are occasionally used therewith, the patient's age, body weight, general health conditions, sex and diet, administration time, administration route, excretion rate of the composition, duration of treatment, various factors including drugs used in combination or simultaneously with the specific compositions, and similar factors well known in the medical field.

Hereinafter, the present invention will be described in more detail with reference to the following Examples. However, these Examples are for illustrative purposes only and the scope of the invention is not limited by these Examples.

Preparation Example: Preparation of Long-Acting Conjugate of Glucagon Derivative Peptide The long-acting conjugate of glucagon derivative peptide was prepared in the following method.

An maleimide-PEG-aldehyde (Japan NOF Inc.), which is a linearly modified polyethylene glycol with a molecular weight of 10 kDa, in which the hydrogens at both terminals are substituted with a 3-(3-maleimidopropionamido)propyl group and a 3-oxopropyl group (propionaldehyde group), respectively, was allowed to react with a derivative having a cysteine among the above-described glucagon derivative peptides to PEGylate the cysteine residue of the glucagon derivative peptide at the maleimide end of maleimide-PEG-aldehyde. Specifically, the glucagon derivative peptide of SEQ ID NO: 37 and the maleimide-PEG-aldehyde were reacted at a molar ratio of 1:1 to 5 at a protein concentration of 3 mg/mL to 10 mg/mL at low temperature for 1 to 3 hours. In particular, the reaction was performed in an environment in which 20% to 60% isopropanol was added to 50 mM Tris buffer (pH 7.5). Upon completion of the reaction, the reaction solutions were applied to SP Sepharose HP (GE Healthcare, USA) to purify the glucagon derivative which was mono-PEGylated on cysteine.

The immunoglobulin Fc fragment was prepared using the immunoglobulin Fc fragment (49.8 kDa, a homodimer in which two chains of SEQ ID NO: 51 are linked by an intra-disulfide bond) having a hinge region of the Pro-Ser-Cys-Pro sequence at the N-terminus by the method described in International Patent Publication No. WO2007/021129.

Then, the purified mono-PEGylated glucagon derivative peptide and the immunoglobulin Fc were reacted at a molar ratio of 1:2 to 10 at a protein concentration of 10 mg/mL to 50 mg/mL at 4° C. to 8° C. for 12 to 18 hours. The reaction was performed in an environment in which 10 mM to 50 mM sodium cyanoborohydride (a reducing agent) and 10% to 20% isopropanol were added to 100 mM potassium phosphate butter (pH 6.0). Upon completion of the reaction, the reaction solutions were applied to the Butyl Sepharose FF purification column (GE Healthcare, USA) and Source ISO purification column (GE Healthcare, USA) to purify the long-acting conjugate of the glucagon derivative peptide in which the polyethylene glycol end at the aldehyde side of the mono-PEGylated glucagon derivative peptide is linked to the nitrogen at the N-terminal proline of one of the two chains of the immunoglobulin Fc homodimer.

After the preparation, the purity analyzed by reverse phase chromatography, size exclusion chromatography, and ion exchange chromatography was shown to be 95% or more.

In particular, the conjugate, in which the glucagon derivative peptide and the immunoglobulin Fc fragment are linked through PEG, was designated as the "long-acting conjugate of the glucagon derivative peptide".

Example 1: Evaluation of Stability of Long-Acting Conjugate of Glucagon Derivative Peptide According to pH and Types of Saccharides or Sugar Alcohols The stability of the long-acting conjugate of the glucagon derivative peptide (hereinafter, "glucagon derivative") was compared under various pH and stabilizers based on a liquid formulation consisting of buffering agent, polysorbate 20 as a surfactant, a saccharide, or a sugar alcohol, and methionine.

The long-acting conjugate of the glucagon derivative peptide obtained in Preparation Example above was prepared as a liquid formulation using the composition shown in Table 1 (the concentration of the long-acting conjugate is 187.09 nmol/mL) and stored at 25° C. for 6 weeks, and then the stability was analyzed by ion-exchange high-performance liquid chromatography (IE-HPLC) and reverse-phase high-performance liquid chromatography (RP-HPLC).

In Table 2, IE-HPLC (%) and RP-HPLC (%) indicate the percentage of the ratio of the area % at the time of measurement divided by the initial area % during the preservation test (area %/start area %), indicating the residual ratio from the initial concentration (187.09 nmol/mL) of the long-acting conjugate of the glucagon derivative.

TABLE 1

| | Buffering agent | pH | saccharide or Sugar alcohol | Isotonic agent | Surfactant | Other |
|---|---|---|---|---|---|---|
| Comparative Example 1 | 20 mM sodium citrate | 4.5 | 5% mannitol | — | 0.02% polysorbate 20 | 0.1 mg/mL methionine |
| Comparative Example 2 | 20 mM sodium citrate | 4.5 | 5% sorbitol | — | 0.02% polysorbate 20 | 0.1 mg/mL methionine |
| Comparative Example 3 | 20 mM sodium citrate | 4.5 | 8% sucrose | — | 0.02% polysorbate 20 | 0.1 mg/mL methionine |
| #1 | 20 mM sodium citrate | 5.0 | 5% mannitol | — | 0.02% polysorbate 20 | 0.1 mg/mL methionine |
| #2 | 20 mM sodium citrate | 5.5 | 5% mannitol | — | 0.02% polysorbate 20 | 0.1 mg/mL methionine |
| #3 | 20 mM sodium citrate | 6.0 | 5% mannitol | — | 0.02% polysorbate 20 | 0.1 mg/mL methionine |
| #4 | 20 mM sodium citrate | 5.0 | 5% sorbitol | — | 0.02% polysorbate 20 | 0.1 mg/mL methionine |
| #5 | 20 mM sodium citrate | 5.5 | 5% sorbitol | — | 0.02% polysorbate 20 | 0.1 mg/mL methionine |
| #6 | 20 mM sodium citrate | 6.0 | 5% sorbitol | — | 0.02% polysorbate 20 | 0.1 mg/mL methionine |
| #7 | 20 mM sodium citrate | 5.0 | 8% sucrose | — | 0.02% polysorbate 20 | 0.1 mg/mL methionine |
| #8 | 20 mM sodium citrate | 5.5 | 8% sucrose | — | 0.02% polysorbate 20 | 0.1 mg/mL methionine |

TABLE 2

| | IE-HPLC (%) | | | RP-HPLC (%) | | |
|---|---|---|---|---|---|---|
| | Initial | 4 weeks | 6 weeks | Initial | 4 weeks | 6 weeks |
| Comparative Example 1 | 100 | 92.3 | N/D* | 100 | 99.6 | N/D |
| Comparative Example 2 | 100 | 92.0 | N/D | 100 | 99.3 | N/D |
| Comparative Example 3 | 100 | 91.4 | N/D | 100 | 99.2 | N/D |
| #1 | 100 | 87.1 | 83.6 | 100 | 100 | 98.3 |
| #2 | 100 | 70.9 | 64.1 | 100 | 95.3 | 93.3 |
| #3 | 100 | 46.3 | 38.3 | 100 | 88.2 | 84.9 |
| #4 | 100 | 86.3 | 81.5 | 100 | 100.3 | 98.7 |
| #5 | 100 | 69.7 | 70.1 | 100 | 95.0 | 93.6 |
| #6 | 100 | 47.6 | 47.4 | 100 | 92.8 | 90.6 |
| #7 | 100 | 87.4 | 87.4 | 100 | 101.8 | 100.6 |
| #8 | 100 | 70.5 | 70.6 | 100 | 97.2 | 96.5 |

*N/D: Analysis not possible due to protein precipitation

As can be seen from the above results, it was confirmed that the formulations (#1, #4, #7) having a composition of sodium citrate and pH 5.0 showed stability.

Additionally, when mannitol, sorbitol, and sucrose, which are saccharides or sugar alcohols that may be included to increase storage stability of a formulation having a composition of sodium citrate and pH 5.0, were included at 5%, 5%, and 8%, respectively, similar stability was shown. In the case of Comparative Examples 1, 2, and 3 having a pH of 4.5, it was confirmed that precipitation occurred at 6 weeks.

Example 2: Evaluation of Stability of Long-Acting Conjugate of Glucagon Derivative According to Types of Buffering Agents, Saccharides, or Sugar Alcohols The stability of the long-acting conjugate of the glucagon derivative was compared according to the types of buffering agents and pH based on the composition of the liquid formulation (sodium citrate, polysorbate 20, and methionine). Among these, the stability of the long-acting conjugate of the glucagon derivative according to mannitol, sorbitol, and sucrose confirmed in Example 1 was compared. In particular, the concentrations of mannitol, sorbitol, and sucrose were selected in consideration of the maximum allowable range of commercially available formulations and that recommended by the licensing agency.

The long-acting conjugate of the glucagon derivative peptide obtained in the Preparation Example above was prepared as a liquid formulation using the composition shown in Table 3 (the concentration of the long-acting conjugate is 187.09 nmol/mL) and stored at 25° C. for 7 weeks, and then the stability was analyzed by ion-exchange high-performance liquid chromatography (IE-HPLC) and reverse phase high-performance liquid chromatography (RP-HPLC).

In Table 4, IE-HPLC (%) and RP-HPLC (%) indicate the percentage of the ratio of the area % at the time of measurement divided by the initial area % during the preservation test (area %/start area %), indicating the residual ratio from the initial concentration (187.09 nmol/mL) of the long-acting conjugate of the glucagon derivative.

TABLE 3

| | Buffering agent | pH | Saccharide or Sugar alcohol | Isotonic agent | Surfactant | Other |
|---|---|---|---|---|---|---|
| #1 | 20 mM sodium citrate | 5.0 | 8% sucrose | — | 0.02% polysorbate 20 | 0.1 mg/mL methionine |
| #2 | 20 mM sodium acetate | 4.5 | 8% sucrose | — | 0.02% polysorbate 20 | 0.1 mg/mL methionine |
| #3 | 20 mM sodium acetate | 5.0 | 8% sucrose | — | 0.02% polysorbate 20 | 0.1 mg/mL methionine |
| #4 | 20 mM sodium acetate | 5.5 | 8% sucrose | — | 0.02% polysorbate 20 | 0.1 mg/mL methionine |
| #5 | 10 mM histidine | 5.5 | 8% sucrose | — | 0.02% polysorbate 20 | 0.1 mg/mL methionine |
| #6 | 10 mM histidine | 6.0 | 8% sucrose | — | 0.02% polysorbate 20 | 0.1 mg/mL methionine |
| #7 | 20 mM sodium citrate | 5.0 | 5% sorbitol | — | 0.02% polysorbate 20 | 0.1 mg/mL methionine |
| #8 | 20 mM sodium acetate | 4.5 | 5% sorbitol | — | 0.02% polysorbate 20 | 0.1 mg/mL methionine |
| #9 | 20 mM sodium acetate | 5.0 | 5% sorbitol | — | 0.02% polysorbate 20 | 0.1 mg/mL methionine |
| #10 | 20 mM sodium acetate | 5.5 | 5% sorbitol | — | 0.02% polysorbate 20 | 0.1 mg/mL methionine |
| #11 | 10 mM histidine | 5.5 | 5% sorbitol | — | 0.02% polysorbate 20 | 0.1 mg/mL methionine |
| #12 | 10 mM histidine | 6.0 | 5% sorbitol | — | 0.02% polysorbate 20 | 0.1 mg/mL methionine |

TABLE 3-continued

| | Buffering agent | pH | Saccharide or Sugar alcohol | Isotonic agent | Surfactant | Other |
|---|---|---|---|---|---|---|
| #13 | 20 mM sodium citrate | 5.0 | 5% mannitol | — | 0.02% polysorbate 20 | 0.1 mg/mL methionine |
| #14 | 20 mM sodium acetate | 4.5 | 5% mannitol | — | 0.02% polysorbate 20 | 0.1 mg/mL methionine |
| #15 | 20 mM sodium acetate | 5.0 | 5% mannitol | — | 0.02% polysorbate 20 | 0.1 mg/mL methionine |
| #16 | 20 mM sodium acetate | 5.5 | 5% mannitol | — | 0.02% polysorbate 20 | 0.1 mg/mL methionine |
| #17 | 10 mM histidine | 5.5 | 5% mannitol | — | 0.02% polysorbate 20 | 0.1 mg/mL methionine |
| #18 | 10 mM histidine | 6.0 | 5% mannitol | — | 0.02% polysorbate 20 | 0.1 mg/mL methionine |

TABLE 4

| | IE-HPLC (%) | | | RP-HPLC (%) | | |
|---|---|---|---|---|---|---|
| | Initial | 4 weeks | 7 weeks | Initial | 4 weeks | 7 weeks |
| #1 | 100 | 94.2 | 87.4 | 100 | 97.7 | 96.3 |
| #2 | 100 | 94.8 | N/D* | 100 | 98.0 | N/D |
| #3 | 100 | 95.0 | 88.1 | 100 | 98.2 | 97.4 |
| #4 | 100 | 93.9 | 85.9 | 100 | 98.2 | 97.8 |
| #5 | 100 | 95.7 | 88.0 | 100 | 98.2 | 97.8 |
| #6 | 100 | 95.3 | 89.0 | 100 | 98.3 | 94.0 |
| #7 | 100 | 94.2 | 87.3 | 100 | 97.6 | 94.9 |
| #8 | 100 | 94.7 | N/D | 100 | 97.7 | N/D |
| #9 | 100 | 95.4 | 89.1 | 100 | 97.8 | 98.1 |
| #10 | 100 | 94.0 | 86.3 | 100 | 98.3 | 97.7 |
| #11 | 100 | 95.5 | 89.1 | 100 | 97.5 | 97.4 |
| #12 | 100 | 94.8 | 88.4 | 100 | 97.3 | 97.3 |
| #13 | 100 | 94.2 | 87.3 | 100 | 97.7 | 97.7 |
| #14 | 100 | 94.8 | N/D | 100 | 97.6 | N/D |
| #15 | 100 | 94.4 | 87.9 | 100 | 97.9 | 98.0 |
| #16 | 100 | 93.7 | 85.6 | 100 | 97.3 | 97.5 |
| #17 | 100 | 94.9 | 87.7 | 100 | 97.4 | 97.2 |
| #18 | 100 | 94.6 | 88.2 | 100 | 97.9 | 97.4 |

*N/D: Analysis not possible due to protein precipitation

As can be seen from the above results, the formulations (#3, #9, #15) having a composition of sodium acetate and pH 5.0 and the formulations (#5, #11, #17) having a composition of histidine and pH 5.5 showed high stability at 25° C. for 7 weeks. However, in the case of the formulations (#2, #8, #14) having a composition of pH 4.5, it was confirmed that precipitation occurred at 7 weeks.

Additionally, when mannitol, sorbitol, and sucrose, which are saccharides or sugar alcohols that may be included to increase storage stability of the long-acting conjugate of the glucagon derivative, were included at 5%, 5%, and 8%, respectively, similar stability was shown.

Example 3: Evaluation of Stability of Long-Acting Conjugate of Glucagon Derivative According to Types of Non-Ionic Surfactants The stability of the long-acting conjugate of the glucagon derivative was compared according to the types of non-ionic surfactants based on the compositions of the liquid formulations (sodium acetate, sucrose, and methionine) confirmed in Example 1 or 2. Among these, the stability of the long-acting conjugate of the glucagon derivative according to mannitol, sorbitol, and sucrose confirmed in Example 1 was compared. In particular, the concentrations of polysorbate 20, polysorbate 80, and poloxamer 188 as non-ionic surfactants were selected in consideration of commercially available formulations.

The long-acting conjugate of the glucagon derivative peptide obtained in Preparation Example above was prepared as a liquid formulation using the composition shown in Table 5 (the concentration of the long-acting conjugate is 187.09 nmol/mL) and stored at 25° C. for 4 weeks, and then the stability was analyzed by ion-exchange high-performance liquid chromatography (IE-HPLC) and reverse-phase high-performance liquid chromatography (RP-HPLC).

In Table 6, IE-HPLC (%) and RP-HPLC (%) indicate the percentage of the ratio of the area % at the time of measurement divided by the initial area % during the preservation test (area %/start area %), indicating the residual ratio from the initial concentration (187.09 nmol/mL) of the long-acting conjugate of the glucagon derivative.

TABLE 5

| | Buffering agent | pH | Saccharide | Isotonic agent | Surfactant | Other |
|---|---|---|---|---|---|---|
| #1 | 20 mM sodium acetate | 5.0 | 8% sucrose | — | 0.02% polysorbate 20 | 0.1 mg/mL methionine |
| #2 | 20 mM sodium acetate | 5.0 | 8% sucrose | — | 0.005% polysorbate 80 | 0.1 mg/mL methionine |
| #3 | 20 mM sodium acetate | 5.0 | 8% sucrose | — | 0.2% poloxamer 188 | 0.1 mg/mL methionine |

TABLE 6

| | IE-HPLC (%) | | | RP-HPLC (%) | | |
|---|---|---|---|---|---|---|
| | Initial | 2 weeks | 4 weeks | Initial | 2 weeks | 4 weeks |
| #1 | 100 | 92.9 | 83.8 | 100 | 99.5 | 95.1 |
| #2 | 100 | 93.2 | 85.4 | 100 | 98.5 | 94.6 |
| #3 | 100 | 92.6 | 84.4 | 100 | 97.5 | 94.5 |

As can be seen from the above results, it was confirmed that the formulations including polysorbate 20, polysorbate 80, and poloxamer 188 as non-ionic surfactants respectively exhibited stability.

Example 4: Evaluation of Stability of Long-Acting Conjugate of Glucagon Derivative According to Presence or Absence of Non-Ionic Surfactants and Amino Acids The stability of long-acting conjugate of the glucagon derivative when the liquid formulation contained or did not contain a non-ionic surfactant or an amino acid stabilizer was compared.

The long-acting conjugate of the glucagon derivative peptide obtained in Preparation Example above was prepared as a liquid formulation using the composition shown in Table 7 (the concentration of the long-acting conjugate is 187.09 nmol/mL) and stored at 25° C. for 4 weeks, and then the stability was analyzed by ion-exchange high-performance liquid chromatography (IE-HPLC) and reverse phase high-performance liquid chromatography (RP-HPLC).

In Table 8, IE-HPLC (%) and RP-HPLC (%) indicate the percentage of the ratio of the area % at the time of measurement divided by the initial area % during the preservation test (area %/start area %), indicating the residual ratio from the initial concentration (187.09 nmol/mL) of the long-acting conjugate of the glucagon derivative.

TABLE 7

| | Buffering agent | pH | Saccharide | Isotonic agent | Surfactant | Other |
|---|---|---|---|---|---|---|
| #1 | 20 mM | 5.0 | 8% sucrose | — | 0.02% polysorbate 20 | 0.1 mg/mL methionine |
| #2 | 20 mM sodium acetate | 5.0 | 8% sucrose | — | — | 0.1 mg/mL methionine |
| #3 | 20 mM sodium acetate | 5.0 | 8% sucrose | — | 0.02% polysorbate 20 | — |
| #4 | 20 mM sodium acetate | 5.0 | 8% sucrose | — | — | — |

TABLE 8

| | IE-HPLC (%) | | | RP-HPLC (%) | | |
|---|---|---|---|---|---|---|
| | Initial | 2 weeks | 4 weeks | Initial | 2 weeks | 4 weeks |
| #1 | 100 | 92.9 | 83.8 | 100 | 99.5 | 95.1 |
| #2 | 100 | 93.0 | 83.7 | 100 | 92.1 | 93.8 |
| #3 | 100 | 88.4 | 74.9 | 100 | 94.6 | 84.2 |
| #4 | 100 | 87.8 | 74.9 | 100 | 92.9 | 82.8 |

As can be seen from the above results, it was confirmed that the formulations (#1, #2) containing amino acids showed stability. In addition, it was confirmed that the formulations containing the non-ionic surfactant and the formulations not including the same exhibited similar stability to each other.

Example 5: Evaluation of Stability of Long-Acting Conjugate of Glucagon Derivative According to pH, Saccharide Concentrations, and Types of Amino Acids The stability of long-acting conjugate of the glucagon derivative was evaluated according to the pH range in which protein foreign matter or precipitation does not occur, the concentration of sucrose as a saccharide, and the types of amino acids other than methionine, based on the compositions (sodium acetate, sucrose, polysorbate 20 and methionine) of the liquid formulations confirmed in Examples 1 to 4.

The long-acting conjugate of the glucagon derivative peptide obtained in Preparation Example above was prepared as a liquid formulation using the composition shown in Table 9 (the concentration of the long-acting conjugate is 187.09 nmol/mL) and stored at 25° C. for 7 weeks, and then the stability was analyzed by ion-exchange high-performance liquid chromatography (IE-HPLC) and reverse phase high-performance liquid chromatography (RP-HPLC).

In Table 10, IE-HPLC (%) and RP-HPLC (%) indicate the percentage of the ratio of the area % at the time of measurement divided by the initial area % during the preservation test (area %/start area %), indicating the residual ratio from the initial concentration (187.09 nmol/mL) of the long-acting conjugate of the glucagon derivative.

TABLE 9

| | Buffering agent | pH | Saccharide | Isotonic agent | Surfactant | Other |
|---|---|---|---|---|---|---|
| #1 | 20 mM sodium acetate | 4.6 | 8% sucrose | — | 0.02% polysorbate 20 | 0.1 mg/mL methionine |
| #2 | 20 mM sodium acetate | 4.8 | 8% sucrose | — | 0.02% polysorbate 20 | 0.1 mg/mL methionine |
| #3 | 20 mM sodium acetate | 5.0 | 8% sucrose | — | 0.02% polysorbate 20 | 0.1 mg/mL methionine |
| #4 | 20 mM sodium acetate | 5.0 | — | — | 0.02% polysorbate 20 | 0.1 mg/mL methionine |
| #5 | 20 mM sodium acetate | 5.0 | 3% sucrose | — | 0.02% polysorbate 20 | 0.1 mg/mL methionine |
| #6 | 20 mM sodium acetate | 5.0 | 5% sucrose | — | 0.02% polysorbate 20 | 0.1 mg/mL methionine |
| #7 | 20 mM sodium acetate | 5.0 | 12% sucrose | — | 0.02% polysorbate 20 | 0.1 mg/mL methionine |
| #8 | 20 mM sodium acetate | 5.0 | 15% sucrose | — | 0.02% polysorbate 20 | 0.1 mg/mL methionine |
| #9 | 20 mM sodium acetate | 5.0 | 8% sucrose | — | 0.02% polysorbate 20 | 0.1 mg/mL arginine |
| #10 | 20 mM sodium acetate | 5.0 | 8% sucrose | — | 0.02% polysorbate 20 | 0.1 mg/mL histidine |
| #11 | 20 mM sodium acetate | 5.0 | 8% sucrose | — | 0.02% polysorbate | 0.1 mg/mL lysine |

TABLE 10

| | IE-HPLC (%) | | | | RP-HPLC (%) RP-HPLC (%) | | | |
|---|---|---|---|---|---|---|---|---|
| | Initial | 2 weeks | 4 weeks | 6 weeks | Initial | 2 weeks | 4 weeks | 6 weeks |
| #1 | 100 | 91.8 | 76.9 | 59.7 | 100 | 90.3 | 84.5 | 74.0 |
| #2 | 100 | 94.4 | 82.1 | 67.6 | 100 | 96.0 | 92.5 | 84.9 |
| #3 | 100 | 95.0 | 83.9 | 70.6 | 100 | 96.8 | 93.2 | 86.2 |
| #4 | 100 | 93.4 | 81.4 | 66.3 | 100 | 94.1 | 91.0 | 83.9 |
| #5 | 100 | 93.8 | 82.0 | 67.4 | 100 | 94.4 | 91.2 | 83.7 |
| #6 | 100 | 94.7 | 83.1 | 69.3 | 100 | 96.5 | 93.0 | 85.2 |
| #7 | 100 | 95.1 | 84.0 | 70.2 | 100 | 96.4 | 93.0 | 86.0 |
| #8 | 100 | 95.1 | 85.2 | 71.6 | 100 | 97.1 | 94.4 | 87.2 |
| #9 | 100 | 93.4 | 82.4 | 69.4 | 100 | 94.6 | 90.7 | 79.0 |
| #10 | 100 | 93.8 | 82.7 | 69.5 | 100 | 95.2 | 91.4 | 80.1 |
| #11 | 100 | 93.9 | 83.1 | 69.5 | 100 | 94.7 | 91.0 | 80.6 |

As can be seen from the above results, when the pH range of the formulation having the composition of sodium acetate as a buffer was pH 4.6 to pH 5.0, the formulation (#3) having the composition of pH 5.0 showed better stability than the other pH compositions. Additionally, in formulation (#1) having a pH of 4.6, small particles were generated when stored at 25° C. for 2 weeks, and the number of small particles increased when stored for 5 weeks. As a result of confirming the stability of the long-acting conjugate of the glucagon derivative according to the concentration of sucrose, when sucrose was contained at 0% (#4) to 15% (#8), the higher the stability was observed as the concentration of sucrose increased.

Additionally, as a result of confirming the stability of the long-acting conjugate of the glucagon derivative according to the types of the amino acids, stability was confirmed in the formulations containing arginine (#9), histidine (#10), and lysine (#11).

That is, these results suggest that the long-acting conjugate of the glucagon derivative has stability in the composition of the liquid formulation of the present invention according to various pH ranges, saccharide concentrations, and types of amino acids.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A liquid formulation of a long-acting conjugate, wherein the liquid formulation comprises:

18 nmol/mL to 936 nmol/mL of a long-acting conjugate of Formula 1 below;

a buffering agent in an amount for maintaining a pH of the liquid formulation in a range of 4.8 to 5.5, wherein the buffering agent is selected from the group consisting of citric acid and a salt thereof, acetic acid and a salt thereof, histidine and a salt thereof, phosphoric acid and a salt thereof, and a combination thereof, wherein the buffering agent is contained at 5 mM to 100 mM for maintaining the pH of the liquid formulation in the range of 4.8 to 5.5; and 5% (w/v) to 8% (w/v) of sucrose;

0.01% (w/v) to 0.1% (w/v) of a non-ionic surfactant, wherein the non-ionic surfactant is polysorbate;

0.01 mg/mL to 1 mg/mL of a stabilizer selected from methionine or histidine; and wherein the liquid formulation does not comprise an isotonic agent:

X—La—F [Formula 1]

in Formula 1 above,

L is a polyethylene glycol linker;

a is 1;

F is an immunoglobulin Fc fragment;

— represents a covalent bond, wherein the glucagon derivative peptide is any one amino acid sequence selected from SEQ ID NO: 17, 22, 23, 24, 29, 33, 35, 36, 37, 38, 40, 41, 42 and 44.

2. The liquid formulation of claim 1, wherein the glucagon derivative peptide is SEQ ID NO: 37.

3. The liquid formulation of claim 1, wherein the X is amidated at the C-terminus; and/or wherein the X is linked via a sulfur atom of cysteine.

4. The liquid formulation of claim 1, wherein the immunoglobulin Fc fragment is derived from IgG4.

5. The liquid formulation of claim 1, wherein the Fis a structure in which two polypeptide chains are linked by a disulfide bond, and are linked only through a nitrogen atom in one of the two chains.

6. The liquid formulation of claim 5, wherein the Fis linked through a nitrogen atom of proline at the N-terminus thereof.

7. The liquid formulation of claim 1, wherein the F is an Fc fragment comprising two polypeptide chains each comprising the amino acid sequence of SEQ ID NO: 51, wherein the two chains are linked by at least one disulfide bond between cysteine residues.

8. The liquid formulation of claim 1, wherein the immunoglobulin Fc fragment and the X are non-glycosylated.

9. The liquid formulation of claim 1, wherein a formula weight of the ethylene glycol repeating unit moiety in the L is in a range of 1 kDa to 100 kDa.

10. The liquid formulation of claim 1, wherein the buffering agent is acetic acid and a salt thereof.

11. The liquid formulation of claim 1, wherein the liquid formulation comprises:

90 nmol/mL to 562 nmol/mL of a peptide conjugate of Formula 1;

5 mM to 25 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5;

5% (w/v) to 8% (w/v) of sucrose;

0.01% (w/v) to 0.1% (w/v) of a non-ionic surfactant, wherein the non-ionic surfactant is polysorbate 20; and 0.01 mg/mL to 1 mg/mL of a stabilizer selected from methionine or histidine.

12. The liquid formulation of claim 1, wherein the liquid formulation comprises:

90 nmol/mL to 562 nmol/mL of a peptide conjugate of Formula 1;

10 mM to 20 mM of a buffering agent selected from citric acid and a salt thereof, acetic acid and a salt thereof, histidine and a salt thereof, phosphoric acid and a salt thereof, and a combination thereof so that the pH of the liquid formulation is 4.8 to 5.5;

5% (w/v) to 8% (w/v) of sucrose;

0.01% (w/v) to 0.1% (w/v) of a non-ionic surfactant, wherein the non-ionic surfactant is polysorbate 20; and 0.01 mg/mL to 1 mg/mL of a stabilizer selected from methionine or histidine.

* * * * *